United States Patent
Kajiki

(10) Patent No.: US 10,180,619 B2
(45) Date of Patent: Jan. 15, 2019

(54) TERAHERTZ WAVE GENERATING ELEMENT AND TERAHERTZ WAVE DETECTING ELEMENT

(71) Applicant: CANON KABUSHIKI KAISHA, Tokyo (JP)

(72) Inventor: Kousuke Kajiki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 267 days.

(21) Appl. No.: 15/027,361

(22) PCT Filed: Sep. 24, 2014

(86) PCT No.: PCT/JP2014/076232
§ 371 (c)(1),
(2) Date: Apr. 5, 2016

(87) PCT Pub. No.: WO2015/053138
PCT Pub. Date: Apr. 16, 2015

(65) Prior Publication Data
US 2016/0246158 A1  Aug. 25, 2016

(30) Foreign Application Priority Data

Oct. 9, 2013 (JP) .................................. 2013-212295
Sep. 8, 2014 (JP) .................................. 2014-182737

(51) Int. Cl.
*G02F 1/37* (2006.01)
*G02F 1/35* (2006.01)
(Continued)

(52) U.S. Cl.
CPC .............. *G02F 1/37* (2013.01); *G01N 21/55* (2013.01); *G02F 1/3534* (2013.01); *G02F 1/365* (2013.01);
(Continued)

(58) Field of Classification Search
CPC .......... G02F 1/37; G02F 1/3534; G02F 1/365; G02F 2203/13; G02F 2001/374; G02F 2001/3503; G02F 2203/023; G01N 21/55
(Continued)

(56) References Cited

U.S. PATENT DOCUMENTS

2004/0238760 A1* 12/2004 Linfield .................... G02F 1/35
250/493.1
2007/0160093 A1* 7/2007 Nishizawa ............ G02F 1/3534
372/21

(Continued)

FOREIGN PATENT DOCUMENTS

JP      02-081035 A    3/1990
JP      2010-204488 A  9/2010

OTHER PUBLICATIONS

International Search Report and Written Opinion for PCT/JP2014/076232, dated Feb. 5, 2015.

*Primary Examiner* — David Porta
*Assistant Examiner* — Gisselle Gutierrez
(74) *Attorney, Agent, or Firm* — Canon USA, Inc. I.P. Division

(57) ABSTRACT

A terahertz wave generating element includes a nonlinear optical crystal generating terahertz waves by propagating light, and a coupling member propagating the generated terahertz waves. The coupling member includes a reflecting face reflecting at least part of the generated terahertz waves. The reflecting face is convex in a propagation direction of the generated terahertz waves. An angle at the coupling member side between the reflecting face and the propagation direction of the light is greater than 90 degrees$-\cos^{-1}$ $(n_g/n_{THz})$ but smaller than 90 degrees at a plane including the light propagation direction. $n_g$ represents a group refractive index of the nonlinear optical crystal at a wavelength of the light, $n_{THz}$ the refractive index of the coupling member at a (Continued)

wavelength of the generated terahertz waves. A curvature radius of the reflecting face, in a reflection region reflecting the radius terahertz waves, is smaller the farther downstream in the light propagation direction.

21 Claims, 14 Drawing Sheets

(51) Int. Cl.
 *G02F 1/365* (2006.01)
 *G01N 21/55* (2014.01)
(52) U.S. Cl.
 CPC ........... *G02F 2001/3503* (2013.01); *G02F 2001/374* (2013.01); *G02F 2203/023* (2013.01); *G02F 2203/13* (2013.01)
(58) Field of Classification Search
 USPC ..................................................... 250/338.1
 See application file for complete search history.

(56) References Cited

U.S. PATENT DOCUMENTS

| | | | |
|---|---|---|---|
| 2010/0213375 A1* | 8/2010 | Loeffler | G02F 1/39 250/339.07 |
| 2012/0032080 A1 | 2/2012 | Koyama et al. | |
| 2012/0032081 A1* | 2/2012 | Itsuji | G01J 3/108 250/340 |
| 2013/0037721 A1* | 2/2013 | Ouchi | G02F 1/3534 250/353 |
| 2013/0240740 A1* | 9/2013 | Ouchi | G01J 5/0818 250/353 |
| 2016/0377958 A1* | 12/2016 | Ouchi | G02F 1/0123 250/353 |
| 2017/0219911 A1* | 8/2017 | Kawase | G02F 1/3501 |

* cited by examiner

TERAHERTZ WAVE GENERATING ELEMENT AND TERAHERTZ WAVE DETECTING ELEMENT

TECHNICAL FIELD

The present invention relates to a terahertz wave generating element which generates terahertz waves, and a terahertz wave detecting element which detects terahertz waves.

BACKGROUND ART

Terahertz waves are electromagnetic waves, having a frequency band component anywhere between 0.03 THz to 30 THz. There are methods to generate terahertz waves using a secondary nonlinear phenomenon by a nonlinear optical crystal. Of these, a technique using electro-optical Cherenkov radiation phenomenon (hereinafter, "Cherenkov radiation") is capable of generating intense and relatively wide bandwidth terahertz waves, which is described in PTL 1.

Cherenkov radiation is a phenomenon where generated terahertz waves 1302 are conically emitted like shock waves, as illustrated in FIG. 13. Cherenkov radiation occurs in a case where the propagating group velocity of light 1301 propagating through a nonlinear optical crystal is faster than the propagating phase velocity of the terahertz waves 1302. Now, an angle $\theta_c$ between the propagation direction of the generated terahertz waves 1302 and the propagation direction of the light 1301 propagating through the nonlinear optical crystal (hereinafter referred to as "Cherenkov angle") can be expressed as $$\cos\theta_c = n_g/n_{THz} \qquad (1)$$

where $n_g$ is the group refractive index of the nonlinear optical crystal as to light, and $n_{THz}$ is the refractive index of the medium through which the terahertz waves propagate as to the terahertz waves.

In cases of using such a terahertz wave generating element employing Cherenkov radiation as a terahertz wave generating source in an information acquiring apparatus to acquire information regarding a specimen using terahertz waves, or the like, wavefront shaping may be necessary. PTL 2 discloses a method for second harmonic generation of light propagating through a nonlinear optical crystal, and shaping and externally extracting the generated second harmonic waves using a collimator, as illustrated in FIG. 14.

Second harmonic waves 1405 generated by light 1404 propagating through the nonlinear optical crystal 1402 is emitted in a conical form, and reflected at a reflecting face 1406 of a coupling member 1403. At this time, the wavefront 1408 of the reflected second harmonic waves 1405 is collimated to a high level of planarity. This configuration shapes the wavefront 1408 of second harmonic waves 1405 to be planar, making the second harmonic waves 1405 easier to handle.

CITATION LIST

Patent Literature

PTL 1 Japanese Patent Laid-Open No. 2010-204488
PTL 2 Japanese Patent Laid-Open No. 02-081035

In a case of applying the configuration according to PTL 2 to a terahertz wave generating element, shaping of the generated terahertz waves can be realized, but distortion in power distribution of the terahertz waves at the wavefront 1408 may increase in some cases. Increased distortion in power distribution results in the effective beam diameter being small even if the terahertz waves are converged, so this is not suitable for transmission or measurement.

SUMMARY OF INVENTION

Solution to Problem

A terahertz wave generating element includes a nonlinear optical crystal configured to generate terahertz waves by light propagating therethrough, and a coupling member through which the terahertz waves generated by the nonlinear optical crystal propagate. The coupling member includes a reflecting face configured to reflect at least a part of the terahertz waves generated by the nonlinear optical crystal. The reflecting face is convex in a propagation direction of the terahertz waves generated by the nonlinear optical crystal. An angle at the coupling member side between the reflecting face and a propagation direction of the light is greater than 90 degrees $-\cos^{-1}(n_g/n_{THz})$ but smaller than 90 degrees at a plane including the propagation direction of the light, where $n_g$ represents a group refractive index of the nonlinear optical crystal at a wavelength of the light, and $n_{THz}$ represents the refractive index of the coupling member at a wavelength of the terahertz waves generated by the nonlinear optical crystal. A radius of curvature of the reflecting face, in a reflection region where the terahertz waves generated by the nonlinear optical crystal are reflected, is smaller the farther downstream in the propagation direction of the light.

Further aspects of the present invention will become apparent from the following description of exemplary embodiments with reference to the attached drawings.

DESCRIPTION OF EMBODIMENTS

First Embodiment

Figure 1:
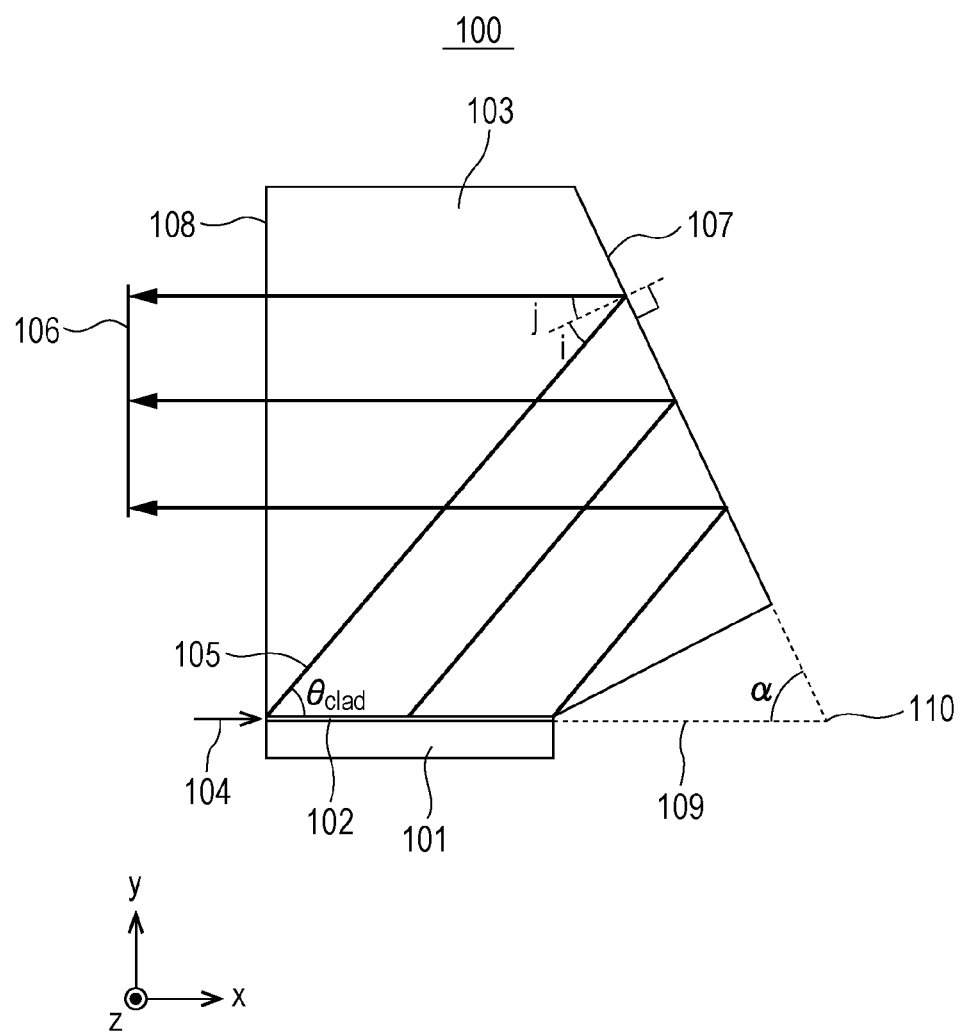
FIG. 1 is a diagram for describing the configuration of a terahertz wave generating element according to a first embodiment.

The configuration of a terahertz wave generating element 100 (hereinafter, also referred to as "element 100") according to a first embodiment will be described with reference to FIG. 1. FIG. 1 is a cross-sectional view of the element 100 with regard to a plane (first plane) including the propagation direction of light 104. Specifically, FIG. 1 is a cross-sectional view at a face including the propagation direction of the light 104 and also perpendicular to the surface of a nonlinear optical crystal. Note that the "propagation direction of the light 104" as used in the present specification refers to a direction in which incident light 104 to the nonlinear optical crystal is substantially propagated, and is defined as a straight line connecting the center of gravity of the input face and the center of gravity of the output face of the nonlinear optical crystal.

The element 100 includes a substrate 101, a nonlinear optical crystal 102 (hereinafter, also referred to as "crystal 102"), and a coupling member 103. The substrate 101 includes a Y-cut lithium niobate (LiNbO$_x$, hereinafter referred to as "LN crystal").

A waveguide 201 including the crystal 102 is formed on the substrate 101. Terahertz waves are generated when light 104 is input to the crystal 102. An ultrashort pulse laser having a pulse width in the range of 1 fs to 100 fs is used as the light 104 input to the crystal 102. More specifically, femtosecond laser is input to the crystal 102. Note that the term "femtosecond laser" as used in the present specification is ultrashort pulse laser having a pulse width in the range of 1 fs to 100 fs.

The wavelength of the light 104 is preferably included in a range of 0.2 μm to 10 μm. Light having a wavelength shorter than 0.2 μm is vacuum ultraviolet light, and is not suitable for use in atmosphere conditions. 10 μm is the wavelength of light obtained with a common carbon dioxide laser. The configuration of the waveguide 201 will be described in detail later.

The coupling member 103 is a member to externally extract generated terahertz waves 105 from the element 100, and includes a reflecting face 107. Details of the configuration of the coupling member 103 will be described later.

The element 100 according to the present embodiment generates terahertz waves 105 by inputting light 104 from the edge face of the crystal 102 and propagating the light 104. The generating terahertz waves 105 are conically emitted by Cherenkov radiation (electro-optical Cherenkov radiation phenomenon), propagate through the coupling member 103, and are externally extracted. While the terahertz waves 105 emitted from the crystal 102 are drawn as straight lines, in reality the terahertz waves 105 are refracted at the time of entering the coupling member 103 from the waveguide 201.

Figure 2:
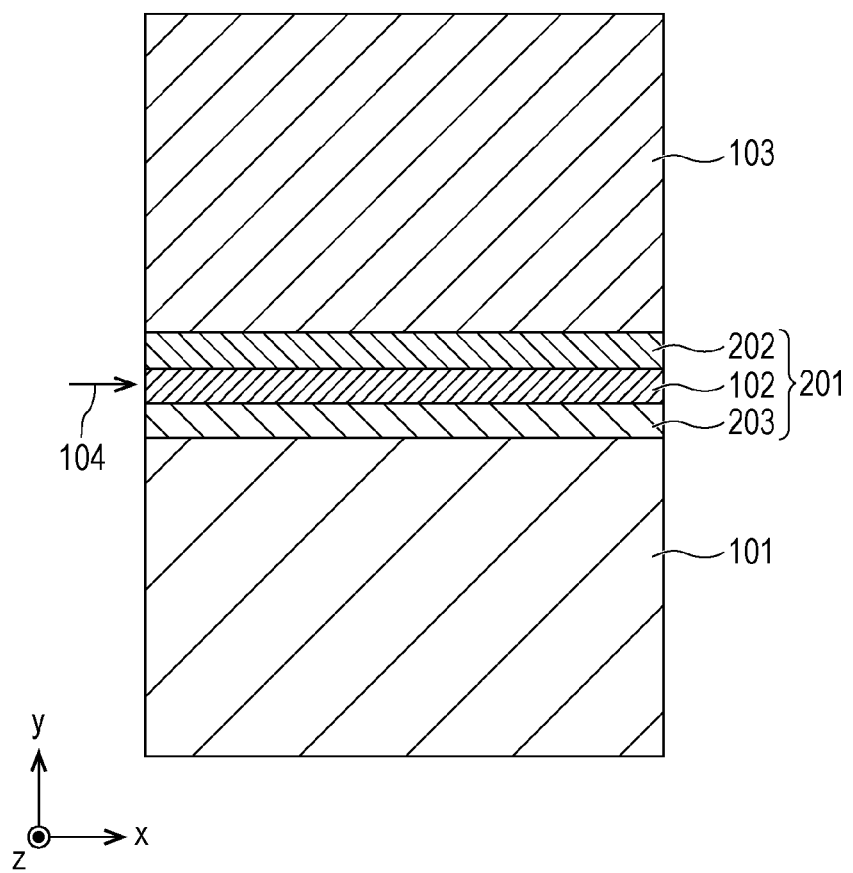
FIG. 2 is a diagram for describing the configuration of waveguide of a terahertz wave generating element according to the first embodiment.

The configuration of the waveguide 201 will now be described with reference to FIG. 2. FIG. 2 is a diagram for describing the configuration of the waveguide 201 according to the present embodiment, and is an enlarged view of around the crystal 102 in FIG. 1. The waveguide 201 includes the crystal 102 serving as a core layer, an upper clad layer 202 formed upon the core layer 102, and a lower clad layer 203 formed below the core layer 102. Note that in the present specification, the upper side of the core layer 102 is the side thereof toward the coupling member 103, and the lower side of the core layer 102 is the side thereof toward the substrate 101.

The core layer 102 is the portion where terahertz waves are generated, and includes an LN crystal which is a nonlinear optical crystal. The type of nonlinear optical crystal is not restricted to an LN crystal, rather, a variety of nonlinear optical crystals may be used, including LiTaO$_x$, NbTaO$_x$, KTP, DAST, ZnTe, GaSe, GaAs, and the like. The thickness of the core layer 102 is preferably half or less the equivalent wavelength of the highest frequency terahertz waves 105 externally emitted, at the core layer 102.

The x axis of the LN crystal of the core layer 102 is configured to correspond to the propagation direction of the light 104, and the y axis to a direction perpendicular to the nonlinear optical crystal. The light 104 has z-axial direction linearly-polarized waves orthogonal to the x axis and y axis.

This configuration improves generation of terahertz waves by the secondary nonlinear phenomenon, and improves efficiency of Cherenkov radiation. That is to say, the crystal axis settings of the LN crystal are chosen such that phase matching is realized between the light 104 and terahertz waves 105, and the phase matching condition is satisfied regarding wave vectors of the light 104 and terahertz waves 105.

The upper clad layer 202 and lower clad layer 203 are layers having lower refractive indices than the core layer 102. Incident light 104 to the core layer 102 is trapped within the core layer 102 between the upper clad layer 202 and lower clad layer 203. Accordingly, the light 104 propagates through the core layer 102 without exiting the waveguide 201.

The substrate 101 and an MgO-doped LN crystal serving as the core layer 102 are bonded by an adhesive agent, such that the adhesive agent functions as the lower clad layer 203 in the present embodiment. The upper clad layer 202 is an adhesive agent for bonding the core layer 102 and the coupling member 103. Note that the configuration of the waveguide 201 is not restricted to this configuration, and clad layers may be provided around the core layer 102 by bonding thereto other materials, having lower refractive indices than the core layer 102, instead of the adhesive agent, for example.

The upper clad layer 202 is suitably formed of thin film of derivatives such as $SiO_x$ or $SiN_x$ or the like, or thin film of resins such as polyethylene terephthalate (PET), and so forth, having lower refractive indices than the LN crystal. The upper clad layer 202 is preferably thick enough to function as a clad layer but sufficiently thin to where the effects of multiple reflection and loss is negligible when externally extracting the terahertz waves from the coupling member 103.

Specifically, in a case where part of the light 104 propagating through the core layer 102 leaks out into the upper clad layer 202, it is sufficient for the intensity of light at the interface of the upper clad layer 202 and coupling member 103 to be $1/e^2$ or less that of the intensity of light at the core layer 102. The thickness of the upper clad layer 202 is preferably around 1/10 or less the equivalent wavelength of the highest frequency terahertz waves 105 to be externally emitted, at the upper clad layer 202. The reason is that generally, if the thickness of this structure is 1/10 or less the wavelength of the electromagnetic waves, the effects of reflection, scattering, refraction, and so forth can be considered to be negligible with regard to the electromagnetic waves.

That is to say, the thickness d of the upper clad layer 202 preferably satisfies $a<d<\lambda_{eq}/10$, where a represents a thickness where the intensity of light at the interface of the upper clad layer 202 and coupling member 103 is $1/e^2$ or less that of the intensity of light at the core layer 102, and $\lambda_{eq}$ represents equivalent wavelength of a wavelength equivalent to the maximum frequency of the terahertz waves 105 at the upper clad layer 202. It should be noted, however, that terahertz waves can be generated using thicknesses other that that described above.

Also, $a<d$ is preferably satisfied regarding the lower clad layer 203, so that the lower clad layer 203 functions as a clad layer regarding the light 104. In a case of a configuration where the terahertz waves 105 are emitted to the lower portion of the core layer 102, the thickness of the lower clad layer 203 also preferably satisfies the condition of $a<d<\lambda_{eq}/10$, in the same way as with the upper clad layer 202.

The waveguide 201 can be formed by regions having lower refractive indices than the core layer 102 being formed above and below the core layer 102, and the techniques for forming the waveguide 201 and the configurations thereof are not restricted in particular. That is to say, the technique is not restricted to bonding together members having different refractive indices using adhesive agent, and for example a technique for forming the waveguide 201 by diffusion or the like on a part of the substrate 101 using an LN crystal, may be used.

The width of the core layer 102 in the lateral direction (z-axial direction) is preferably small, taking into consideration generation of terahertz waves by the nonlinear effect. The reason is that in principle, the power density of generated terahertz waves 105 is proportionate to the square of the power density of the light 104 (the peak power density in a case where the light is a pulsed laser).

The waveguide 201 according to the present embodiment is a ridged waveguide where the lateral width of the core layer 102 is smaller than the wavelength of the terahertz waves to be generated, formed by a method where the portion to serve as the core layer 102 is imparted a high refractive index so as to have a difference in refractive index with the surrounding regions, a method where resin or the like is embedded around the core layer 102, or the like. Moreover, an arrangement may be made where, instead of providing different clad layers around the core layer 102 as in the present embodiment, clad layers above, below, and to the sides, may be formed as an integral configuration.

If the width of the core layer 102 is too small, this may result in reduced coupling efficiency at the time of the light 104 entering the core layer 102, increased waveguide loss, and so forth. Accordingly, the width of the core layer 102 is preferably no less than the center wavelength of the light 104 and no more than ten times this figure. Note that the term "center wavelength" means a wavelength in the spectrum of the light 104 where the intensity (amplitude) is the greatest.

The width of the core layer 102 is also preferably a width where the input light 104 can propagate through the core layer 102 in single mode. The reason is that if the light 104 propagates through the core layer 102 in multi-mode, the peak intensity of the light 104 decreases due to mode dispersion as the propagation proceeds, leading to lower efficiency in the conversion to terahertz waves 105. Further, depending on the output of the light 104, phenomena such as optical damage or the like may occur at the LN crystal, so the width of the core layer 102 has to be determined taking this point into consideration as well.

If optical damage occurs at the crystal 102 due to the output of the light 104 being strong, multiple waveguides may be provided so as to input the light 104 in a divided manner. An arrangement may also be made where multiple waveguides of different structures and materials are provided, and the light 104 is input to the waveguides so as to generate terahertz waves 105 having intended properties.

Further, interference may be caused among terahertz waves generated from multiple waveguides, so as to adjust the beam form and beam direction of the terahertz waves. Such a configuration should be made so that the terahertz waves to be extracted do not cancel each other out by interference. The way in which the multiple waveguides are arrayed is not restricted in particular; multiple waveguides may be arrayed in the z direction or y direction, or in a non-parallel manner. Further, a slab waveguide may be applied where the core layer 102 extends laterally in a uniform manner.

Next, the configuration of the coupling member 103 will be described. The material used for the coupling member 103 is one where the terahertz waves 105 are not totally reflected at the interface of the waveguide 201 and the coupling member 103, but rather can be extracted as traveling waves within the coupling member 103, and one where loss of the terahertz waves 105 is small. An example of a material which satisfies these conditions is high-resistance silicon (Si).

The coupling member 103 has a shape which is convex in the propagation direction of the terahertz waves 105 generated from the crystal 102, and has a reflecting face 107 which reflects and corrects at least part of the generated terahertz waves. The expression to "collect" terahertz waves is defined as suppressing the dispersion of the terahertz waves as compared to before reflection, such as making the dispersing terahertz waves parallel, and so forth, in addition to converging the terahertz waves.

The reflecting face 107 is arranged such that the angle between the propagation direction of the light 104 and the reflecting face 107 of the coupling member 103 at a plane including the propagation direction of the light 104, that is to say the magnitude of inclination a of the reflecting face 107 as to the direction of propagation of the light 104, satisfies $$90 \text{ degrees} - \theta_{clad} < \alpha < 90 \text{ degrees} \quad (2)$$

where $\theta_{clad}$ is the Cherenkov angle at the coupling member 103, and from Expression (1), $\theta_{clad} = \cos^{-1}(n_g/n_{THz})$. Also, $n_g$ is group refractive index of the crystal 102 with regard to light, and $n_{THz}$ is the refractive index of the crystal 102 with regard to the terahertz waves.

Note that while the first plane includes the propagation direction of the light 104 and is perpendicular to the surface of the crystal 102 in the present embodiment, the present invention is not restricted to this, so it is sufficient for the first plane to include the propagation direction of the light 104, and inclination as to the substrate 101 or waveguide 201 is not restricted in particular. This configuration results in the terahertz waves 105 reflecting at the reflecting face 107 and being emitted from a transmission face 108.

Also, in a case where the reflecting face 107 is provided so as to satisfy Expression (3), the terahertz waves 105 do not transmit the reflecting face 107 but are totally reflected. Particularly, in a case where the reflecting face 107 satisfies Expression (4), the wavefront 106 of the terahertz waves 105 reflected at the reflecting face 107 can be shaped so as to be planar.

$$\alpha \geq \sin^{-1}(n_e/n_{THz}) + 90 \text{ degrees} - \theta_{clad} \quad (3)$$

$$\alpha = 90 \text{ degrees} - \theta_{clad}/2 \pm \lambda/8 \quad (4)$$

where $n_e$ is the external refractive index of the coupling member 103, and $\lambda$ is the wavelength of the terahertz waves generated from the nonlinear optical crystal.

In this case, the incident angle i of the terahertz waves 105 to the reflecting face 107, and the reflection angle j when reflecting, satisfy Expression (5). Note that the incident angle of terahertz waves in the present specification is the angle between the generated terahertz waves input to the reflecting face and a perpendicular to the reflecting face. The reflection angle is the angle between the terahertz waves reflected at the reflecting face and a perpendicular to the reflecting face.

$$i = j = \theta_{clad}/2 \quad (5)$$

An LN crystal is used for the crystal (core layer) 102 and high-resistance silicon (Si) is used for the coupling member 103 in the present embodiment, so according to Expression (1), the Cherenkov angle at the waveguide 201 is approximately 65 degrees. The terahertz waves 105 refract at the time of input to the coupling member 103 from the waveguide 201, and the Cherenkov angle $\theta_{clad}$ at the coupling member 103 is approximately 50 degrees. The element 100 is configured such that the angle $\alpha$ between the propagation direction of the light 104 and the reflecting face 107 at the first plane is 65 degrees, which satisfies Expression (4).

FIGS. 3A through 3D are examples of cross-sectional views at a face (second plane) orthogonal to the propagation direction of the light 104 in the terahertz wave generating element 100 according to the present embodiment. At least part of the cross-section of the reflecting face 107 of the coupling member 103 at the second plane includes a curve which is concave at the crystal 102 side, i.e., a curve which is convex toward the propagation direction of the terahertz waves 105, with the center of the curve being in the propagation direction of the light 104.

The reflecting face 107 of the coupling member 103 is configured such that the length thereof at a cross-section orthogonal to the propagation direction of the light 104 is longer the farther upstream in the propagation direction of the light 104, within a reflection region where the terahertz waves 105 are reflected. In other words, the radius of curvature of the reflecting face 107 in the reflection region where the terahertz waves 105 are reflected is smaller the farther downstream in the propagation direction of the light 104.

Specifically, in the reflection region where the terahertz waves 105 are reflected, the radius of curvature at a cross-section which passes through a first position and is orthogonal to the propagation direction of the light 104, is longer than the radius of curvature at a cross-section which passes through a second position and is orthogonal to the propagation direction of the light 104. Accordingly, the length of the reflecting face 107, at a cross-section which passes through the first position in the propagation direction of the light 104 and is orthogonal to the propagation direction of the light 104, is longer than the length of the reflecting face 107 at a cross-section which passes through the second position which is downstream of the first position in the propagation direction of the light 104 and is orthogonal to the propagation direction of the light 104.

That is to say, the reflecting face 107 is configured such that the optical power at the reflecting region, reflecting the terahertz waves generated downstream in the propagation direction of the light 104, is greater than the optical power at the reflecting region reflecting the terahertz waves generated upstream in the propagation direction of the light 104. This configuration enables distortion in power distribution of the terahertz waves 105 generated at the crystal 102 to be reduced.

Figure 3A:
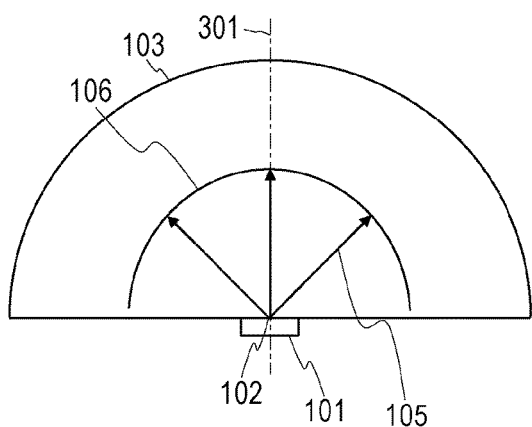
FIGS. 3A through 3D are cross-sectional views taken along a plane orthogonal to the propagation direction of light in the terahertz wave generating element according to the first embodiment.

One example is a configuration where a cross-section at the second plane has a curve such as an arc or the like, as illustrated in FIG. 3A. In this case, the wavefront of the terahertz waves 105 emitted to the coupling member 103 is emitted conically with the first plane 301 as a plane of symmetry, the terahertz waves 105 can be shaped by reflection at the reflecting face 107.

Figure 3B:
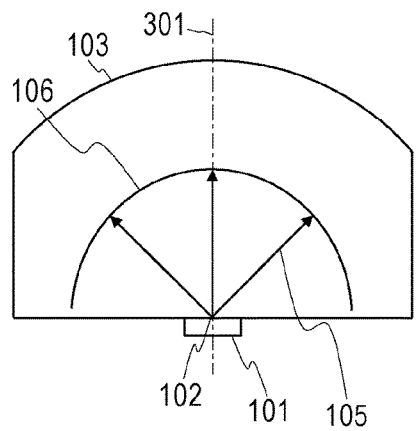
Figure 3C:
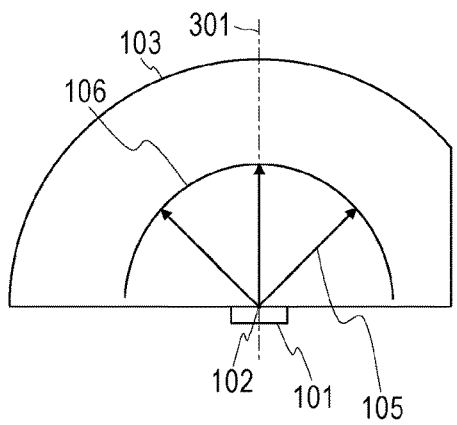
Figure 3D:
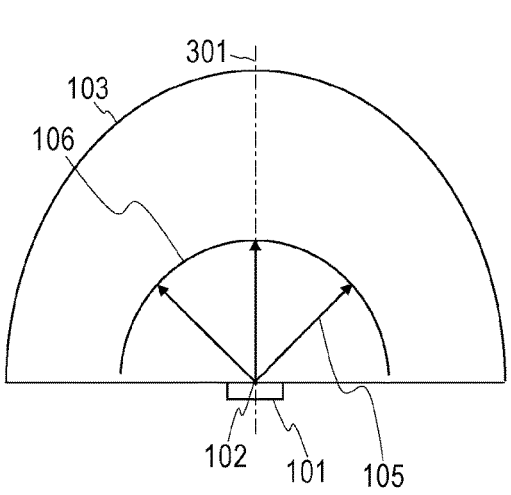

The present invention is not restricted to the above example, and a configuration where a part of the arc which is the curve is missing, or the like, such as illustrated in FIGS. 3B and 3C, can be applied as well. In this case, an arrangement is made where a region where the power of the generated terahertz waves 105 is small corresponds to the missing portion, is terahertz waves with substantially greater power can be formed and extracted. Also, a configuration including an ellipse such as illustrated in FIG. 3D enables forming a beam converging in the z-axial direction of the crystal 102. These and various other forms may be made.

Note that the reflecting face 107 may be symmetrical with the first plane 301 as a plane of symmetry, in cross-section at a plane orthogonal to the propagation direction of the light 104, or may be asymmetric as illustrated in FIG. 3C.

The reflecting face 107 according to the present embodiment is a shape including a part of a conical face of which the propagation direction of the light 104 is the axis. The propagation direction of the light 104 and the axis of the conical face preferably match at a precision of equivalent wavelength of the terahertz waves 105 or finer. The present invention is not restricted to this arrangement though, and a shape including a part of a curved face obtained by rotating any straight line or curve on the propagation direction of the light 104 as the axis thereof, or the like, is applicable.

The terahertz waves 105 reflected at the reflecting face 107 are transmitted through the transmission face 108 of the coupling member 103 and externally emitted. While the present embodiment describes the terahertz waves 105 as perpendicularly entering the transmission face 108, this is not restrictive. For example, Fresnel loss due to reflection can be reduced by causing the terahertz waves 105 to be transmitted through the transmission face 108 at Brewster's angle (16.3 degrees in a case where the coupling member 103 is formed of silicon). The coupling member 103 may further include another reflecting face, separate from the reflecting face 107.

Power distribution of the terahertz waves 105 generated using the element 100 will be described. Power distribution in a terahertz wave generating element 1400 (hereinafter referred to as "element 1400") using the collimator according to PTL 2 as a coupling member 103 will be described for the sake of comparison.

Figure 14:
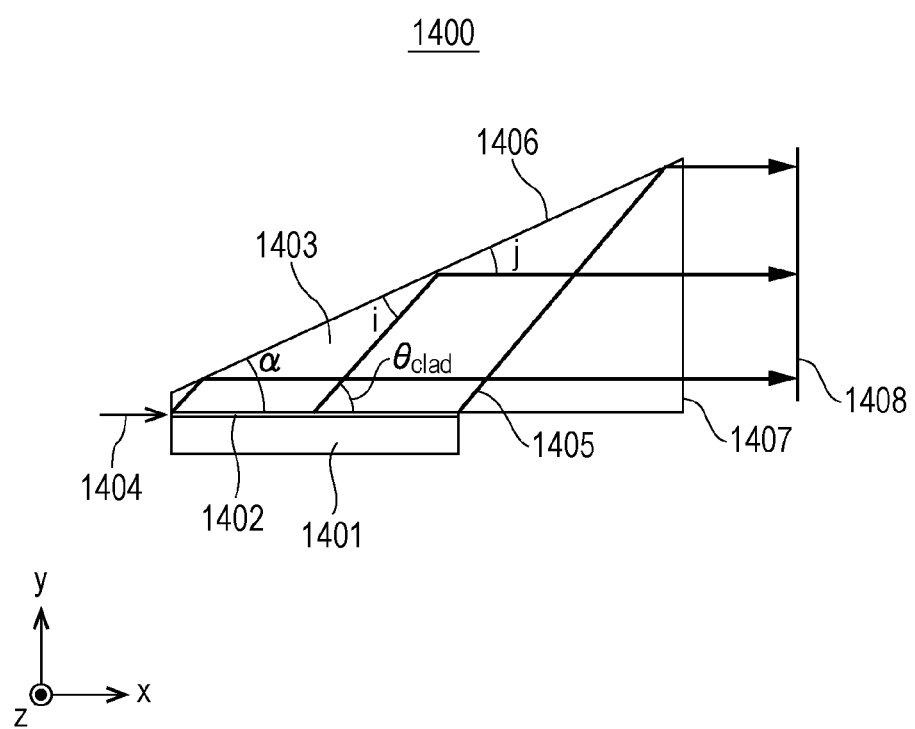
FIG. 14 is a diagram for describing the configuration of a second harmonic generation element according to the related art.

The configuration of the element 1400 to which PTL 2 has been applied is illustrated in FIG. 14. Note that while PTL 2 generates second harmonic waves from light 1404 entering a nonlinear optical crystal 1402 (hereinafter referred to as "crystal 1402"), this is replaced with a configuration to generate terahertz waves in accordance with the present embodiment, in the following description. While the generation principles of second harmonic waves and terahertz waves in a nonlinear optical crystal are different as such, these are the same with regard to the fact that electromagnetic waves are omitted from a waveguide by Cherenkov phase matching.

The element 1400 to which the related art has been applied includes a substrate 1401 having the crystal 1402 and a coupling member 1403, and the coupling member 1403 has a reflecting face 1406. A member which functions as a clad layer is interposed between the crystal 1402 and the coupling member 1403. At least a part of a primary portion of the reflecting face 1406 which reflects the terahertz waves 1405 generated from the crystal 1402 includes a conical face, the axis of the conical face matching the propagation direction of the light 1404 propagating through the crystal 1402.

Setting the Cherenkov angle $\theta_{clad}$ to 50 degrees, and the refractive index of the coupling member 1403 at the wavelength of the terahertz waves 1405 to 3.42, the half apex angle α of the conical face is 25 degrees, in accordance to the expression ($r=i=j=\theta_{clad}/2$) described in PTL 2. The incident angle i of terahertz waves 1405 to the reflecting face 1406 is 25 degrees, and the reflection angle j is 25 degrees.

Upon the light 1404 entering the crystal 1402, the terahertz waves 1405 generated from the crystal 1402 are reflected at the reflecting face 1406 of the coupling member 1403 and shaped, and travel in the same direction as the propagation direction of the light 1404 through the crystal 1402. The terahertz waves 1405 reflected at the reflecting face 1406 are then emitted externally from the coupling member 1403 by perpendicularly transmitting through the transmission face 1407. The wavefront 1408 of the conically-emitted terahertz waves 1405 is shaped as a plane and externally emitted by this configuration.

Figure 4A:
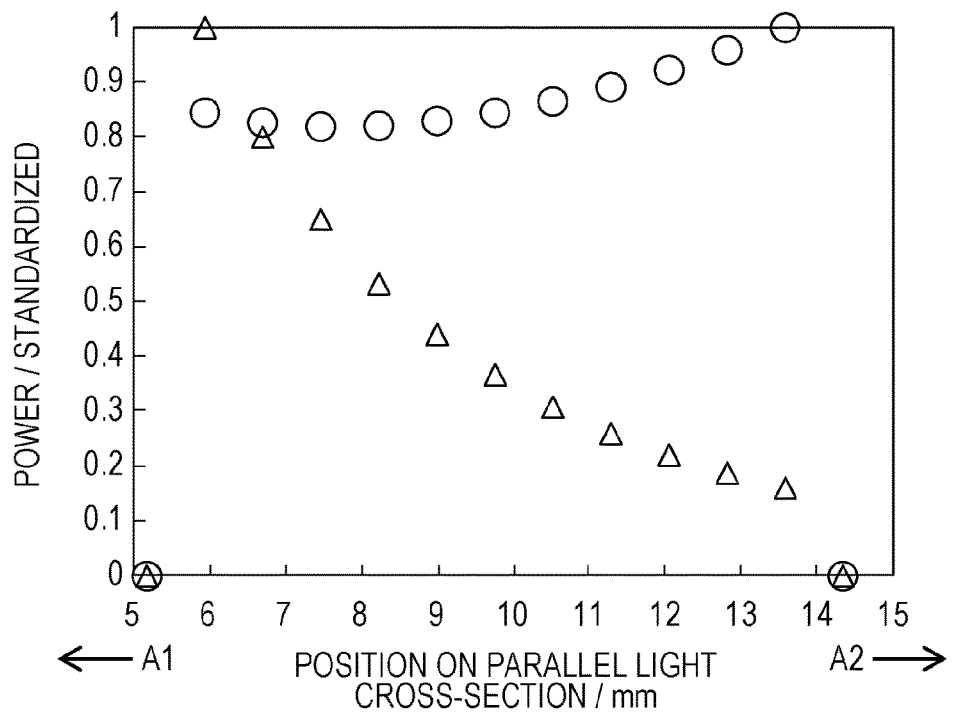
FIGS. 4A and 4B are diagrams illustrating terahertz wave power distribution on a parallel light cross-section.
Figure 4B:
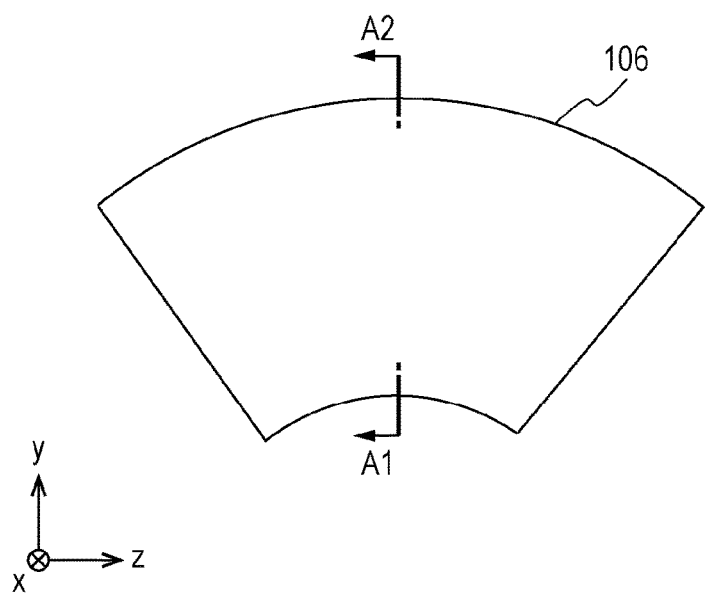

Power distribution of terahertz waves will be described with reference to FIGS. 4A and 4B. FIG. 4B is a diagram viewing the wavefronts 106 and 1408 of the terahertz waves emitted from the respective coupling members 103 and 1403 of the two elements 100 and 1400, from the upstream side in the propagation direction of the light 104 and 1404. FIG. 4A is a power distribution diagram of terahertz waves at various positions on an A1-A2 cross-section in FIG. 4B. The power of the terahertz waves 105 from the element 100 are represented by circles, and the power of the terahertz waves 1405 from the element 1400 are represented by triangles. The horizontal axis in FIG. 4A represents the positions on the A1-A2 cross-section, with the smaller values toward the A1 side and the and larger values toward the A2 side.

It can be seen from FIG. 4A that the power distribution of the terahertz waves 1405 generated at the element 1400 is such that the power of terahertz waves markedly deteriorates toward the A2 side of the A1-A2 cross-section. In comparison, there is little difference in power at any position in the power distribution of the terahertz waves 105 generated by the element 100 according to the present embodiment, so it can be seen that distortion in power distribution is reduced.

When light is input to a waveguide including a nonlinear optical crystal, the power of the light on the waveguide is smaller the farther from the input end of the waveguide. This is due to the pulse width of the light spreading as being propagated over the waveguide. It is known that other varying factors include dispersion due to material, waveguide loss, non-uniformity of the crystal, phase properties of light input to the waveguide, and so forth.

Figure 5:
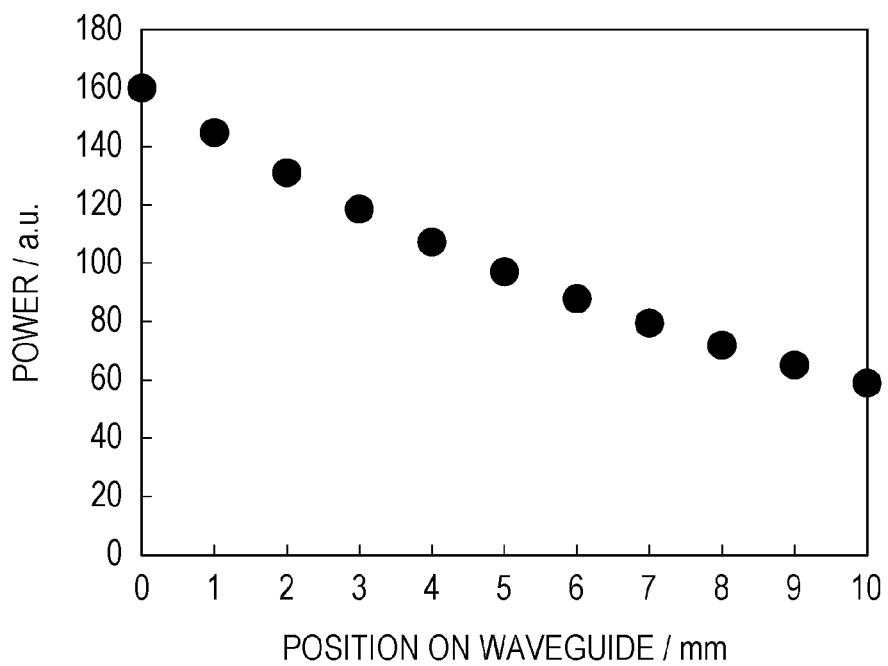
FIG. 5 is a diagram illustrating terahertz wave power distribution on a waveguide.

As the lower of light becomes weaker, the power of terahertz waves generated from the nonlinear optical crystal also becomes weaker as the light propagates through the waveguide. That is to say, the power of terahertz waves becomes smaller toward the downstream side in the propagation direction of the light, exhibiting a power distribution such as illustrated in FIG. 5.

On the other hand, both the reflecting faces 107 and 1406 are part of a conical face, so the length of the reflecting face at a cross-section orthogonal to the propagation direction of the light (hereinafter may be referred to simply as "length of reflecting face") may differ depending on the position where the terahertz waves are reflected. If terahertz waves which have uniform power are input to all positions of the reflecting face, the terahertz waves reflected at positions where the length of the reflecting face is longer will be dispersed and the power will be lower. On the other hand, the terahertz waves reflected at positions where the length of the reflecting face is shorter will have higher density, and the power will be greater than terahertz waves reflected at positions where the length of the reflecting face is longer.

In the case of the element 1400 to which the PTL 2 has been applied, the closer toward the input end side of the crystal 1402 where the light 1404 is input (the upstream side in the propagation direction of the light) the terahertz waves 1405 are generated, the greater the power of these terahertz waves 1405 is, and these are reflected at the shorter-length portions of the reflecting face 1406. The further downstream in the propagation direction of the light 1404 the terahertz waves 1405 are generated, the weaker the power of these terahertz waves 1405 is, and these are reflected at the longer-length portions of the reflecting face 1406. That is to say, the weaker the power of terahertz waves 1405 is, the greater the dispersion at the reflecting face 1406 and deterioration of power density is, so the greater the distortion of power distribution at the A1-A2 cross-section is.

On the other hand, the element 100 according to the present embodiment is configured such that the terahertz waves 105 of which the power is weaker are reflected at portions where the length of the reflecting face 107 is short, and the terahertz waves 105 of which the power is greater are reflected at portions where the length of the reflecting face 107 is long. That is to say, the effect which change in power of the light 104 propagating through the crystal 102 has on the power distribution of the terahertz waves 105, and the effect which the length of the reflecting face 107 has on the power distribution of the terahertz waves 105, are opposite. Thus, the distortion in power distribution of the generated terahertz waves 105 can be reduced.

Second Embodiment

Figure 6:
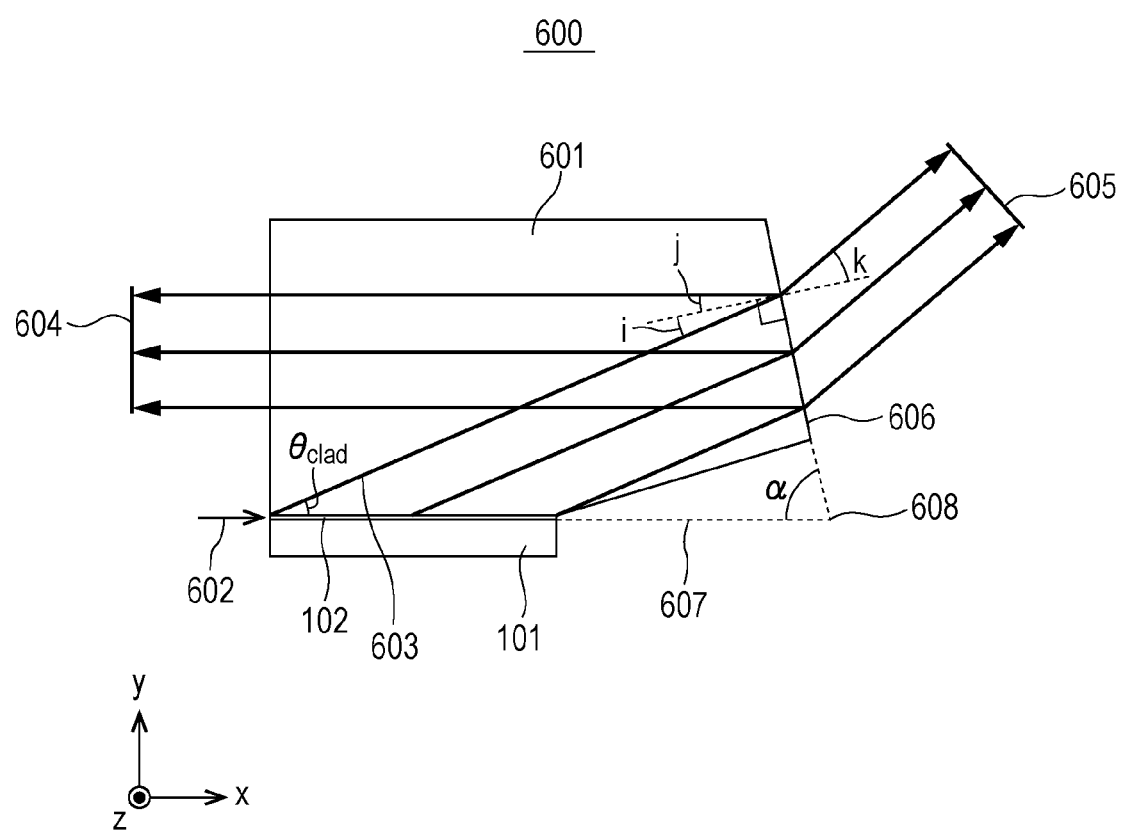
FIG. 6 is a diagram for describing the configuration of a terahertz wave generating element according to a second embodiment.

A terahertz wave generating element 600 (hereinafter referred to as "element 600") according to a second embodiment will be described with reference to FIG. 6. While total reflection of the terahertz waves 105 was performed at the reflecting face 107 of the coupling member 103 in the first embodiment, a reflecting face 606 of a coupling member 601 of the present embodiment transmits part of the generated terahertz waves 603.

The element 600 includes a substrate 101, a waveguide 201 which has a crystal (core layer) 102, and a coupling member 601. The substrate 101 and waveguide 201 are of the same configuration as the first embodiment. Light 602 propagates through the crystal 102 to generate terahertz waves 603.

A diamond material is used for the coupling member 601. Assuming the refractive index of diamond as to terahertz waves around a frequency of 1 THz to be 2.38, according to Expression (1), the Cherenkov angle $\theta_{clad}$ in a case of the generated terahertz waves 605 being emitted at the coupling member 603 is 24 degrees.

Setting the angle α between the reflecting face 606 and the propagation direction of the light so as to satisfy Expression (4) yields an incident angle i of the terahertz waves 603 as to the reflecting face 606 of 12 degrees, and a reflection angle j of 12 degrees from Expression (5). An angle k between the terahertz waves 603 which have transmitted through the reflecting face 606 and a perpendicular to the reflecting face 606 (output angle) is 29 degrees.

The total reflection angle emitted from diamond to the atmosphere is 25 degrees, so total reflection of the terahertz waves 603 at the reflecting face 606 does not occur, and a part is transmitted. Calculation by the Fresnel equations with the polarization of the terahertz waves 603 as linearly polarized light in the z direction yields that the power transmittance of the terahertz waves 603 at the reflecting face 606 is 79%. This transmittance can be optionally adjusted by coating the reflecting face 606 with resin or the like.

The length of the reflecting face 606 at a cross-section which passes through a first position in the propagation direction of the light 602 and is orthogonal to the propagation direction of the light 602, is longer than the length of the reflecting face 606 at a cross-section which passes through a second position downstream from the first position in the propagation direction of the light 602 and is orthogonal to the propagation direction of the light 602. It is sufficient for this condition to be satisfied at reflection regions where the terahertz waves 603 generated from the crystal 102 are reflected. That is to say, the radius of curvature of the reflecting face 606 at reflection regions where the terahertz waves 603 generated from the crystal 102 are reflected is smaller toward the downstream side in the propagation direction of the light 602.

The terahertz waves 603 which have been reflected at the reflecting face 606 or transmitted through the reflecting face 606 are both emitted externally with distortion of power distribution having been reduced. The configuration of the element 600 according to the present embodiment where the coupling member is configured such that part of the generated terahertz waves 603 are transmitted allows terahertz waves 603 which have been shaped and distortion in power distribution reduced, to be branched into two.

The angle α between the propagation direction of the light 602 and the reflecting face 606 of the coupling member 601 is configured so as to satisfy the above-described Expression (4) in the present embodiment. Accordingly, the terahertz waves 603 reflected at the reflecting face 606 are shaped so that the wavefront 605 is planar, and externally emitted. The terahertz waves 603 which have transmitted through the reflecting face 606 are also shaped so that the wavefront 604 is planar, and externally emitted. Thus, according to the present embodiment, multiple outputs of terahertz waves, which have been shaped and power distribution distortion reduced, can be obtained.

The terahertz waves 603 split into two at the reflecting face 606 may be used separately, or the two outputs of terahertz waves 603 may be coaxially joined again after each being emitted form the coupling member 601, subjected to interference and used for detection. This can be used with various types of known interferometers, such as the Michelson interferometer.

Third Embodiment

A third embodiment will now be described. In the first and second embodiments, the terahertz waves 105 generated from the crystal 102 have been described as being externally extracted through the coupling member 103. In a case of use as a terahertz waves generating source in an information acquiring apparatus using terahertz waves, the extracted terahertz waves are guided to a specimen by an optical system and measurement is performed. In comparison, in the present embodiment a specimen 701 is placed at an optional face of the coupling member 103 of an element 100, and the specimen 701 is measured. A configuration where the specimen 701 is disposed on the reflecting face 107 is exemplarily illustrated in FIG. 7A, and a configuration where the specimen 701 is disposed on the transmission face 108 is exemplarily illustrated in FIG. 7B.

The terahertz wave generating element according to the present embodiment has the same configuration as the element 100 according to the first embodiment. That is to say, the element 100 has a substrate 101, crystal 102, and coupling member 103, with light 104 being propagated through the crystal 102 to generate terahertz waves 105, which are emitted to the coupling member 103. The emitted terahertz waves 105 are reflected at the reflecting face 107 of the coupling member 103.

Figure 7A:
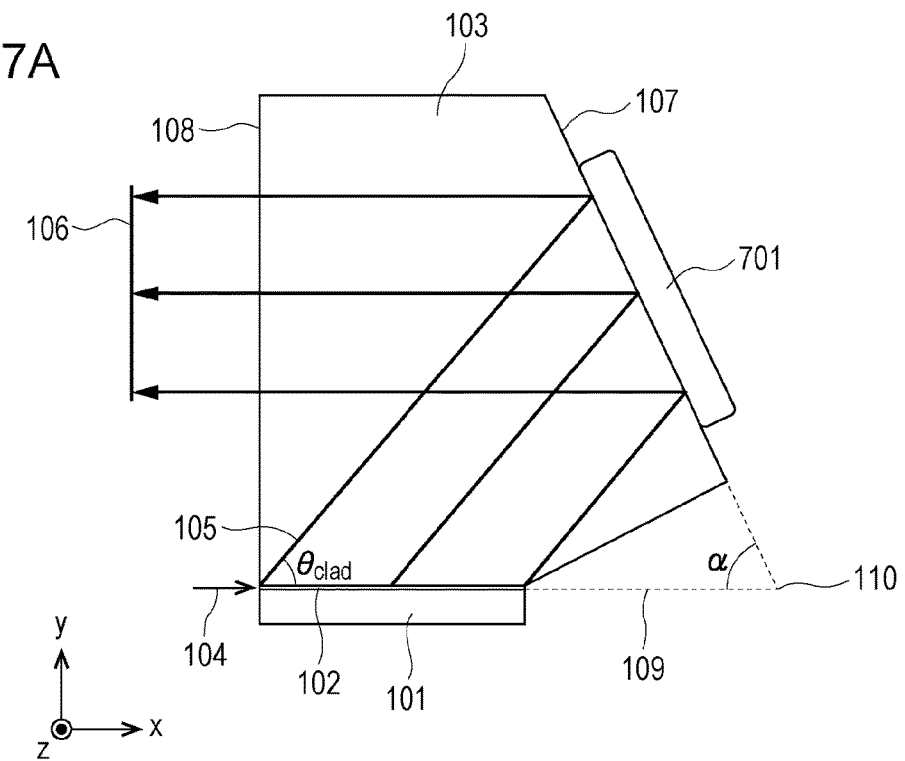
FIGS. 7A and 7B are diagrams for describing the configuration of a terahertz wave generating element according to a third embodiment.
Figure 7B:
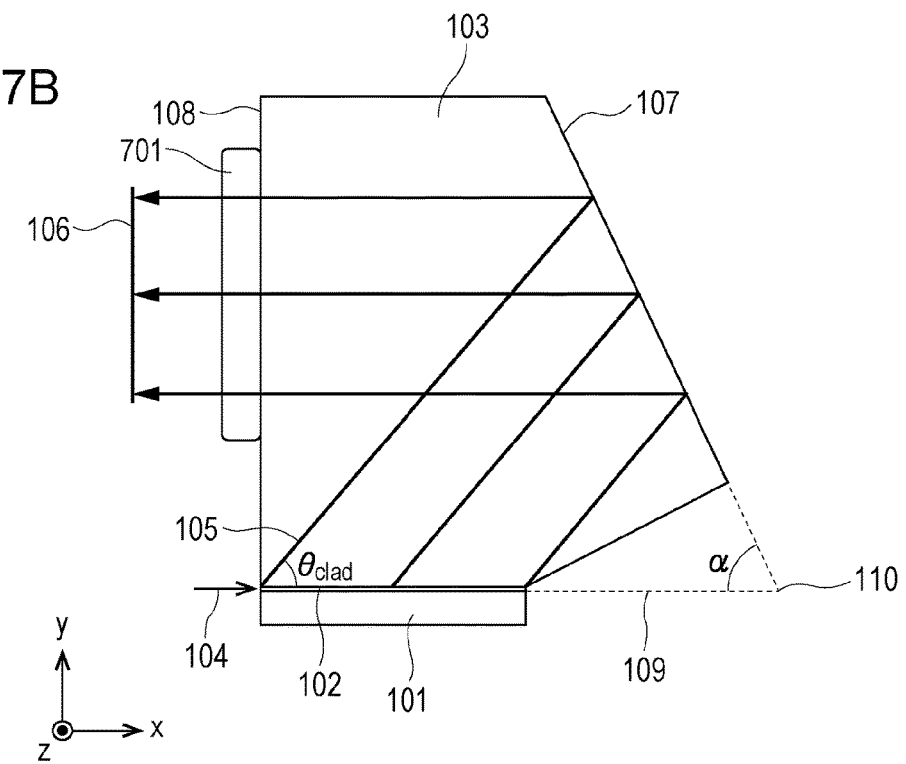

The generated terahertz waves 105 are reflected at the interface of the specimen 701 disposed on the reflecting face 107 and the coupling member 103, and externally emitted, as illustrated in FIG. 7A. Alternatively, a configuration may be made such as illustrated in FIG. 7B, where the specimen 701 is disposed on the transmission face 108, so that the terahertz waves 105 are reflected at the reflecting face 107, and then transmitted through the transmission face 108 and specimen 701 to be externally emitted. Accordingly, the externally emitted terahertz waves 105 are affected by optical properties and the like of the specimen 701, which can be detected and studied to obtain information regarding the specimen 701.

According to the present embodiment, a specimen can be measured using terahertz waves with little distortion in power distribution. This configuration also does away with the need to provide an external optical system and space to irradiate the specimen by the terahertz waves, which can contribute to reduction in size of the information acquiring apparatus.

Fourth Embodiment

Figure 8:
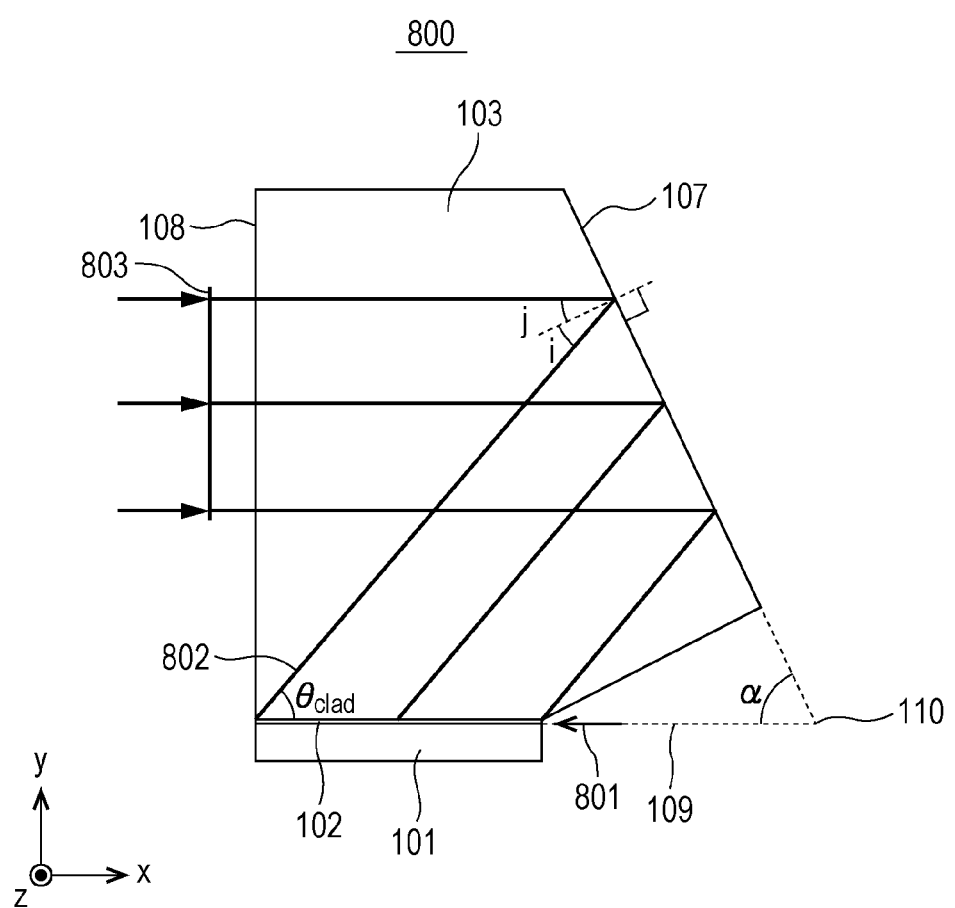
FIG. 8 is a diagram for describing the configuration of a terahertz wave detecting element according to a fourth embodiment.

A terahertz wave generating element 800 (hereinafter referred to as "element 800") according to a fourth embodiment will now be described with reference to FIG. 8. FIG. 8 is a diagram for describing the configuration of the element 800. The element 800 has the same configuration as the element 100 according to the first embodiment. That is to say, the element 800 has a substrate 101, crystal (core layer) 102, and coupling member 103. While the embodiments described above have been with regard to terahertz wave generating elements, the element 800 according to the present embodiment detects terahertz waves 802 which have passed through the coupling member 103 and reached the crystal 102.

Linearly-polarized light 801 is input to the crystal 102 with the polarization thereof at an optionally inclined angle from the z-axis direction of the crystal 102 toward the y-axis direction (e.g., 45 degrees). At this time, the light 801 is input to the crystal 102 from a face facing the face which was used in the first through third embodiments for input of light 104.

Phase difference occurs between the z-axis component and y-axis component in the electric field of the light 801 propagated through the crystal 102 and emitted, due to the birefringent properties of the crystal 102, so the light 801 is elliptically polarized. Such phase difference due to birefringence differs depending on the type of nonlinear optical crystal used as the crystal 102, the direction of incident polarization, the length of the waveguide 201, and so forth. The phase difference can be negated to zero depending on the configuration.

The terahertz waves 802 are input from the transmission face 108 of the coupling member 103 in a state where the wavefront 803 is planar, reflected at the reflecting face 107, and then collected at the crystal 102. The light 801 is being propagated through the crystal 102, there is interaction between the terahertz waves 802 and the light 801 within the crystal 102, according to a process opposite to that of generating terahertz waves 802.

Note that the light 801 is input from the face facing the face from which the light 104 is input in the crystal 102 of the element 100, so the upstream side and downstream side in the propagation direction of the light is opposite to that in the first through third embodiments. The reflecting face is convex in a direction opposite to the propagation direction of the terahertz waves 802 input to the nonlinear optical crystal. The length of the reflecting face 107 at a cross-section which passes through a first position in the propagation direction of the light 801 and is orthogonal to the propagation direction of the light 801, is longer than the length of the reflecting face 107 at a cross-section which passes through a second position upstream from the first position in the propagation direction of the light 801 and is orthogonal to the propagation direction of the light 801. It is sufficient for this configuration to be established at reflection regions where the terahertz waves 802 generated from the crystal 102 are reflected. That is to say, the radius of curvature of the reflecting face 107 at reflection regions where the terahertz waves 802 entering from the transmission face 108 are reflected is greater toward the downstream side in the propagation direction of the light 801.

Upon terahertz waves 802 being input while the light 801 is propagating through the crystal 102, linear electro-optic effect (Pockels effect, a type of secondary nonlinear process) occurs at the crystal 102 due to the electric field of the terahertz waves 802. Accordingly, the refractive index of the z axis of the crystal 102 changes, and the polarization state of the light 801 changes.

AS a result, in addition to the phase difference occurring due to birefringent properties of the crystal 102, phase difference also occurs regarding the z-axis component of the light 801 under the influence of the electric field of the terahertz waves 802. On the other hand, the phase difference occurring regarding the y-axis component of the electric field of the light 801 is only phase difference due to the birefringent properties of the crystal 102. The phase difference occurring regarding the z-axis component of the light 801 and the phase difference occurring regarding the y-axis component differ, so the propagation state of the light 801 omitted from the crystal 102, such as the ellipticity of the elliptic polarization, the direction of the primary axis, and so forth, changes. If this change can be detected by an external polarization element (omitted from illustration) and light detector (omitted from illustration) and so forth, the intensity of the magnetic field of the terahertz waves 802 can be detected.

The light 801 emitted from the crystal 102 may be detected by splitting into two polarized rays using a Wollaston prism, and improving the S/N ratio by differential amplification of two light detectors (omitted from illustration). This improving of the S/N ratio by differential amplification is not essential, so one light detector alone may be employed, using a polarization plate. A phase compensation plate (e.g., quarter wave plate) may be added between the output end of the crystal 102 and a polarizer that is omitted from illustration, for compensation for inductive birefringence.

While the face facing the face used of input of light 104 in the first through third embodiments is used for input of light to the crystal 102 in the present embodiment, light 801 may be input from the same face (end). In this case, the matching length is shorter so signal intensity is weaker.

Also, the present embodiment investigates the effects of terahertz waves 802 using the phenomenon in which the polarization state of light 801 is changed by the linear electro-optic effect by the terahertz waves 802, but the present invention is not restricted to this. Other methods may be used, such as detecting phase change of light 801 propagating through the crystal 102, or detecting light signals of difference frequency of the frequency of the light 801 propagating through the crystal 102 and frequency of the terahertz waves 802, i.e., detecting beat signals of the light, and so forth.

The detection sensitivity of the terahertz waves 802 is dependent on the state of the light 801 and the intensity of the terahertz waves 802. Even if terahertz waves 802 with little distortion in power distribution are input to the coupling member 103 of the element 800, the distortion in power distribution increases by the terahertz waves 802 reflecting off of the reflecting face 107. Accordingly, detection sensitivity can be improved by adjusting the propagation state of the light 801 so that the light 801 is at a suitable state for detection at the position where the power of the terahertz waves 802 is great.

In the present embodiment, the terahertz waves 802 which have transmitted the specimen or reflected at the specimen are guided to the coupling member 103 of the element 800, and input to the crystal 102 via the reflecting face 107. However, this arrangement is not restrictive, and an arrangement may be made where the specimen 901 is situated on any face of the coupling member 103 of the element 800, as illustrated in FIGS. 9A and 9B.

Figure 9A:
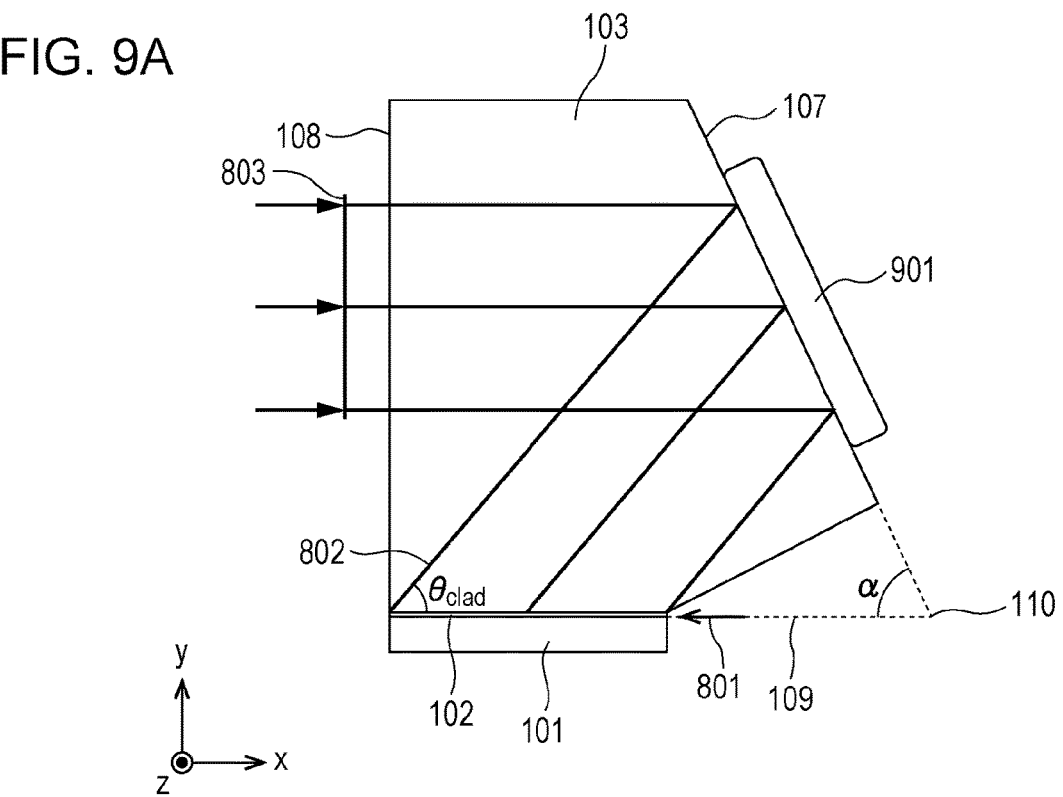
FIGS. 9A and 9B are diagrams for describing another configuration of the terahertz wave detecting element according to the fourth embodiment.
Figure 9B:
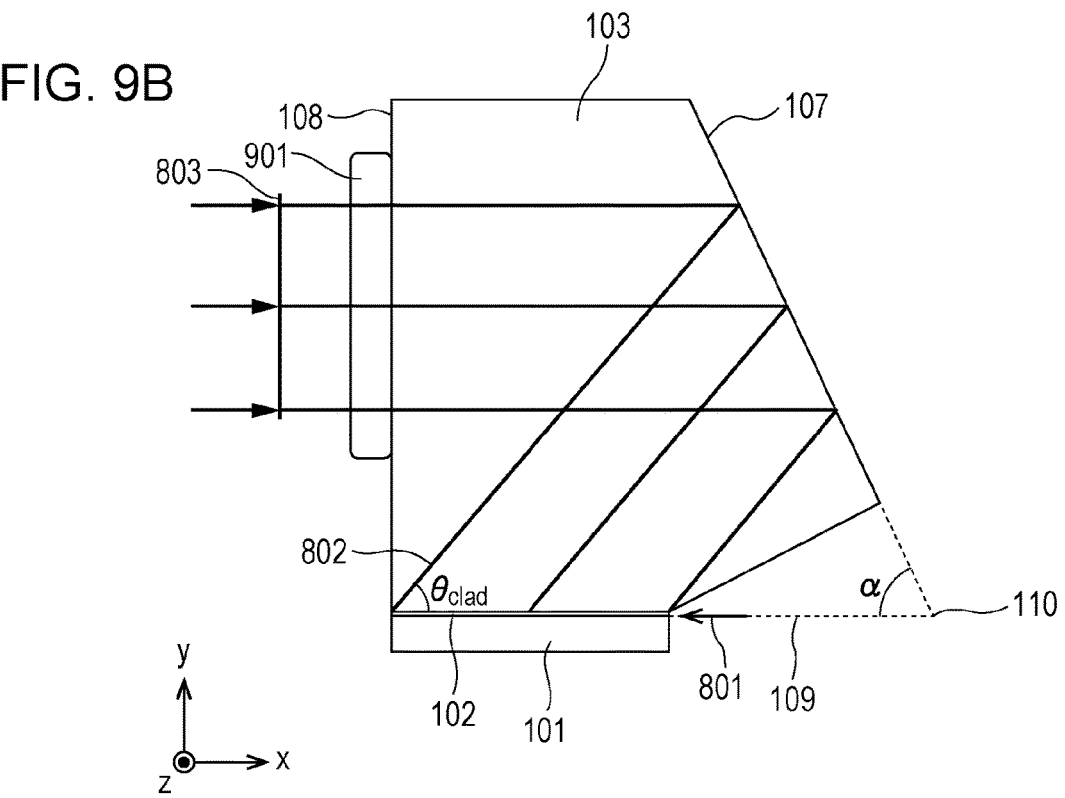

In the arrangement illustrated in FIG. 9A, the terahertz waves 802 which have transmitted through the transmission face 108 from the outside and entered the coupling member 103 are reflected at the interface of the specimen 901 positioned at the reflecting face 107 and the coupling member 103, and then enter the crystal 102. In the arrangement illustrated in FIG. 9B, the terahertz waves 802 which have transmitted through the specimen 901 and transmission face 108 from the outside and entered the coupling member 103 are reflected at the reflecting face 107 and enter the crystal 102. These configurations do away with the need to provide an external optical system and space to guide terahertz waves reflected at or transmitted through the specimen to the detector, which can contribute to reduction in size of the information acquiring apparatus.

Fifth Embodiment

Figure 10A:
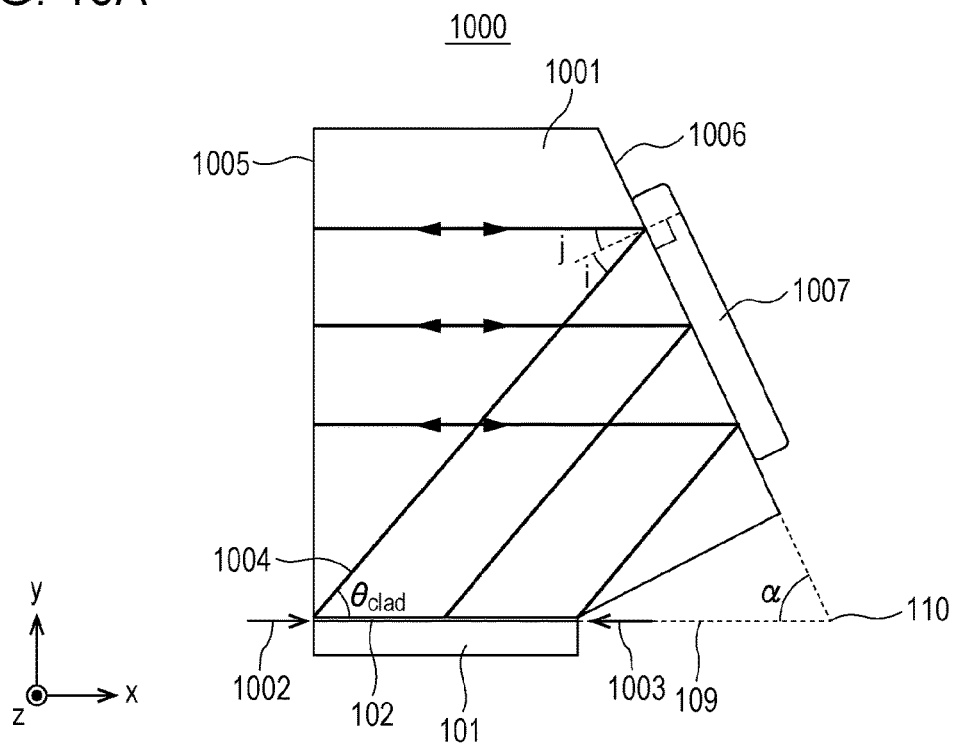
FIGS. 10A and 10B are diagrams for describing the configuration of a terahertz wave detecting element according to a fifth embodiment.

A fifth embodiment will be described with reference to FIG. 10A. FIG. 10A illustrates an example of the configuration of a terahertz wave generating/detecting element 1000 (hereinafter referred to as "element 1000") according to the present embodiment. The elements 100 in the first through third embodiments have been described as having functions to generate terahertz waves, and the element 800 in the fourth embodiment has been described as having functions to detect terahertz waves generated at a separate generating element. On the other hand, the element 1000 according to the present embodiment both generates and detects terahertz waves with a single element.

The element 1000 has a substrate 101, a crystal 102, and a coupling member 1001. The substrate 101 and the waveguide 201 including the crystal 102 are of the same configuration as with the first embodiment. the coupling member 1001 is the same as the coupling member 103 according to the first embodiment with regard to material and shape, but the coupling member 1001 has two reflecting faces 1005 and 1006, whereas the coupling member 103 has the reflecting face 107 and transmission face 108.

Describing the element 1000 in more detail, generating light 1002 propagating through the crystal 102 generates terahertz waves 1004. The generated terahertz waves 1004 propagate through the coupling member 1001, and reflect at the reflecting face 1006 and thus are shaped.

Thereafter, the terahertz waves 1004 are reflected at the reflecting face 1005, reflected again at the reflecting face 1006, and input to the crystal 102. Detection light 1003 for detecting the terahertz waves 1004 is input from a face facing the face from which the light 1002 of the crystal 102 has been input, so the terahertz waves 1004 can be detected in the same way as with the fourth embodiment.

Figure 10B:
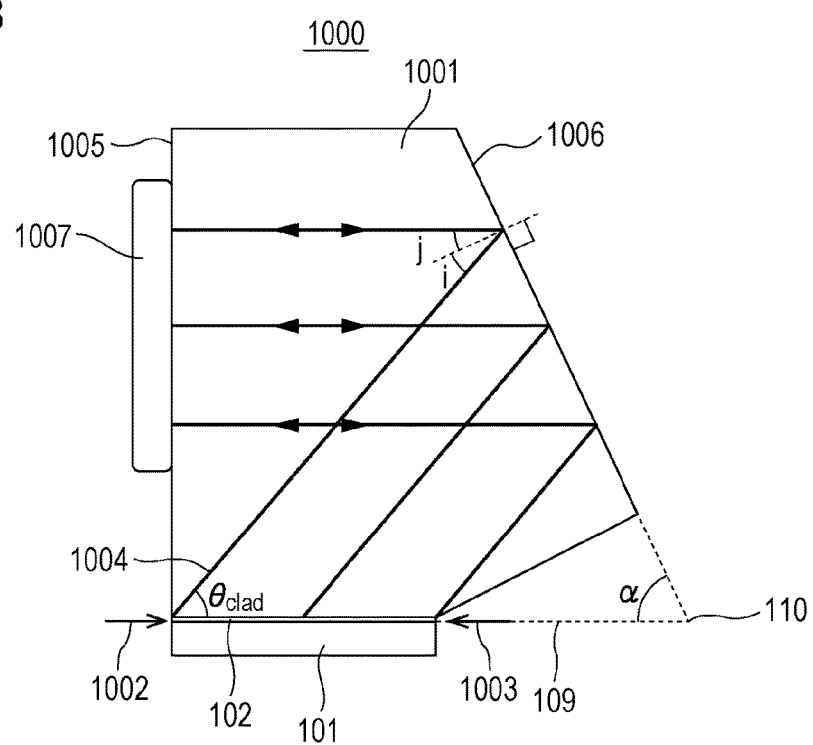

In this case, placing the specimen 1007 at the reflecting face 1006 as illustrated in FIG. 10A allows information of the specimen 1007 to be obtained by detecting the terahertz waves 1004 reflected at the specimen 1007. Alternately, the specimen 1007 may be positioned on the reflecting face 1005, as illustrated in FIG. 10B.

While the configuration of the present embodiment involves providing one waveguide 201 including the crystal 102, a separate waveguide may be provided, so that the generation light 1002 and detection light 1003 are each input from different waveguides. The light source of the generation light 1002 and detection light 1003 may be the same or may be different. In a case where the same light source is to be used, the light from the light source is first split into two by a beam splitter or the like before input to the crystal 102, and then the two are input to the crystal 102. Also, generation light 1002 that was emitted from the crystal 102 without being converted into terahertz waves may be used as detection light 1003.

The element 1000 according to the present embodiment can measure the specimen 1007 with reduced distortion in the power distribution of the generated terahertz waves. The detected terahertz waves 1004 have distortion in power distribution, so detection sensitivity can be improved by adjusting so that the detection light 1003 is in a suitable state for detection at a position where the power of the terahertz waves 1004 input to the crystal 102 is strong.

Further, there is no need to externally provide peripheral optical systems to handle the terahertz waves 1004, so a small-sized generating/detecting element can be provided. Such a terahertz wave generating/detecting element may be applied to small-sized probes, such as endoscopes or the like, and so forth.

Sixth Embodiment

Figure 11:
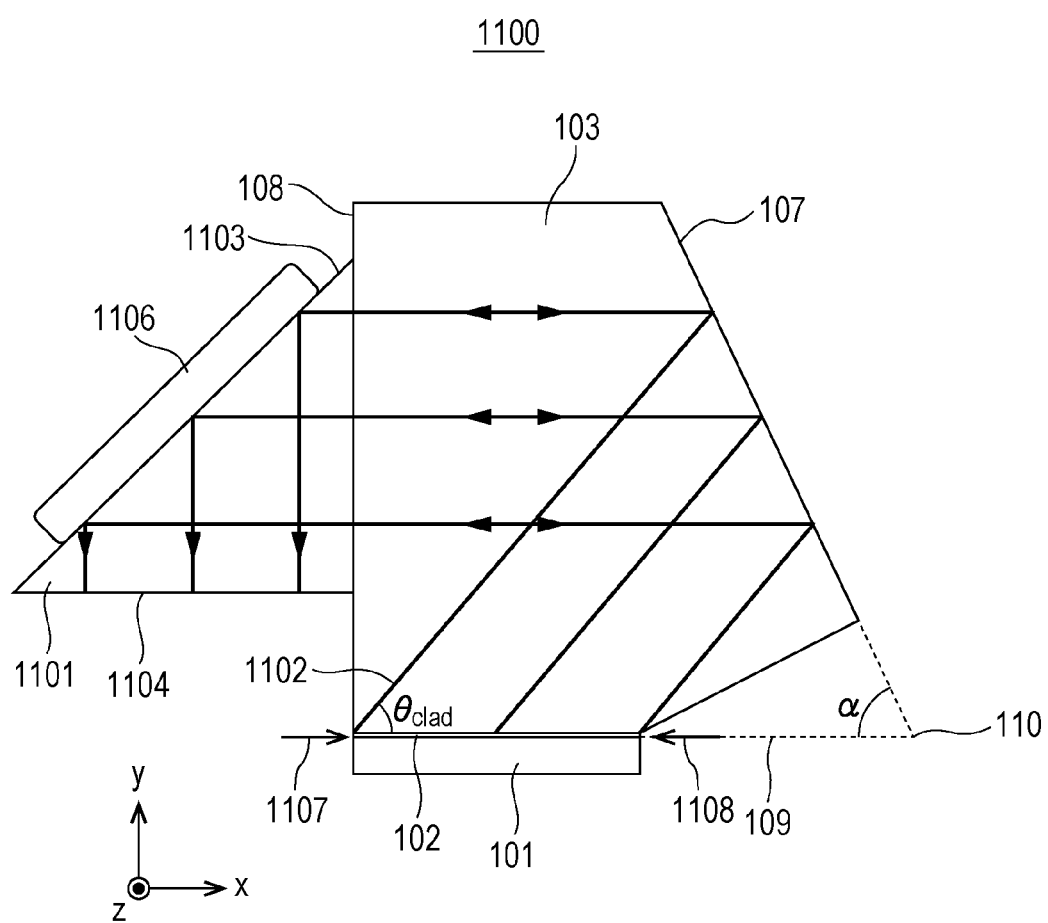
FIG. 11 is a diagram for describing the configuration of a terahertz wave detecting element according to a sixth embodiment.

A modification of the terahertz wave generating element according to the fifth embodiment will be described in the sixth embodiment, with reference to FIG. 11. FIG. 11 is a diagram for describing the configuration of a terahertz wave generating/detecting element 1100 (hereinafter referred to as "element 1100"). The element 1100 is a configuration which further has a triangular prism 1101 added to the configuration of the element 100 according to the first embodiment.

The triangular prism 1101 is disposed in contact with the transmission face 108 of the coupling member 103, and a specimen 1106 is disposed on a total-reflection face 1103 of the triangular prism 1101. The triangular prism 1101 is a prism including Si, and a face 1104 is coated with a conductive material such as metal or the like which reflects terahertz waves well.

The total-reflection face 1103 of the triangular prism 1101 is a face which totally reflects the terahertz waves 1102. If the refractive index of the specimen 1106 is assumed to be 2, the total reflection angle in a case of terahertz waves 1102 being input from the triangular prism 1101 to the specimen 1106 is 36 degrees. The refractive index of the specimen 1106 is assumed to be 2 in the present embodiment, and the incident angle of the terahertz waves 1102 as to the total-reflection face 1103 is set to be 45 degrees, thus making a configuration where there is total reflection of the terahertz waves 1102 at the total-reflection face 1103. Note that the reflection of terahertz waves 1102 at the interface between the coupling member 103 and the triangular prism 1101 is preferably as close to zero as possible.

The element 1100 generates terahertz waves 1102 upon generation light 1107 being input to the crystal 102. The generated terahertz waves 1102 are reflected at the reflecting face 107, upon which power distribution distortion of the terahertz waves 1102 is reduced. Thereafter, the terahertz waves 1102 are transmitted through the transmission face 108 and input to the triangular prism 1101.

The terahertz waves 1102 are propagated through the triangular prism 1101, totally reflected at the interface of the total-reflection face 1103 and the specimen 1106, perpendicularly reflected at the face 1104, and retraces its own path to be input to the crystal 102. Analyzing the detection light 1108 emitted from the crystal 102 enables detection of terahertz waves and information of the specimen 1106 to be obtained, in the same way as with the fourth embodiment.

While the transmission face 108 of the coupling member 103 and the triangular prism 1101 are disposed adjacently in the present embodiment, this is not restrictive, and the coupling member 103 and the triangular prism 1101 may be integrated. Also, the form of the triangular prism 1101 used in the present embodiment is not restricted in particular, as long as the configuration is such that there is total reflection of the terahertz waves 1102 at the total-reflection face 1103 where the specimen 1106 is disposed, and the totally reflected terahertz waves 1102 are input to the crystal 102.

According to the element 1100 of the present embodiment, distortion in power distribution of generated terahertz waves can be reduced. Specimen measurement can also be performed using the terahertz waves with reduced power distribution distortion. Further, there is no need to externally provide peripheral optical systems to handle the terahertz waves, so a small-sized generating/detecting element can be provided.

Seventh Embodiment

Generating single-frequency terahertz waves will be described as a seventh embodiment. In the present embodiment, single-frequency terahertz waves are generated using the element 100 according to the first embodiment. The first embodiment uses ultrashort pulse laser for the light to be input to the crystal 102. Conversely, the terahertz wave generating element according to the present embodiment generates single-frequency terahertz waves by inputting two lights with different oscillation frequencies to the crystal 102.

Examples of light sources which output light of two different oscillation frequencies include neodymium-doped yttrium aluminum garnet (Nd:YAG)-excited potassium titanyl phosphate optical parametric oscillator (KTP-OPO), two wavelength-variable laser diodes, and so forth. Hereinafter, the two light oscillation frequencies will be referred to as ν1 and ν2.

Upon the light of the two different oscillation frequencies ν1 and ν2 being input to the crystal 102, single-frequency terahertz waves 105, equivalent to the differential wave between the oscillation frequency ν1 and the oscillation frequency ν2, are generated. The generated terahertz waves 105 are reflected at the reflecting face 107, reducing distortion in power distribution thereof, in the same way as with the above-described embodiments.

Such a single-frequency terahertz wave generating method can be applied to cases of performing testing or imaging using terahertz waves of a particular frequency, such as testing an inclusion amount of a particular substance in a pharmaceutical product by matching the frequency to the absorption spectrum of that particular substance.

The method for generating single-frequency terahertz waves is not restricted to application to the first embodiment, but rather can be applied the terahertz wave generating devices, detecting devices, and generating/detecting devices according to the second through sixth embodiments. In a case where light having two different oscillation frequencies is input to a nonlinear optical crystal of a terahertz wave detecting element or terahertz wave generating/detecting element, single-frequency terahertz waves, equivalent to the differential wave between the oscillation frequencies ν1 and ν2, can be detected. Changing the frequency difference of the two lights enables detection of amplitude of terahertz waves at a desired frequency.

Eighth Embodiment

Description will be made in an information acquiring apparatus 1200 (hereinafter referred to as "apparatus 1200") using terahertz waves, in an eight embodiment. The apparatus 1200 is a terahertz time-domain spectroscopy (THz-TDS) apparatus which uses the THz-TDS principle to acquire the time waveform of terahertz waves. The apparatus 1200 acquires time waveforms of terahertz waves 1230 reflected at a specimen 1216, as information of the specimen 1216. The optical properties, shape, and other such information of the specimen 1216 can be acquired using the acquired time waveform. An arrangement may also be made where an image is formed based on the obtained information of the specimen 1216.

Figure 12A:
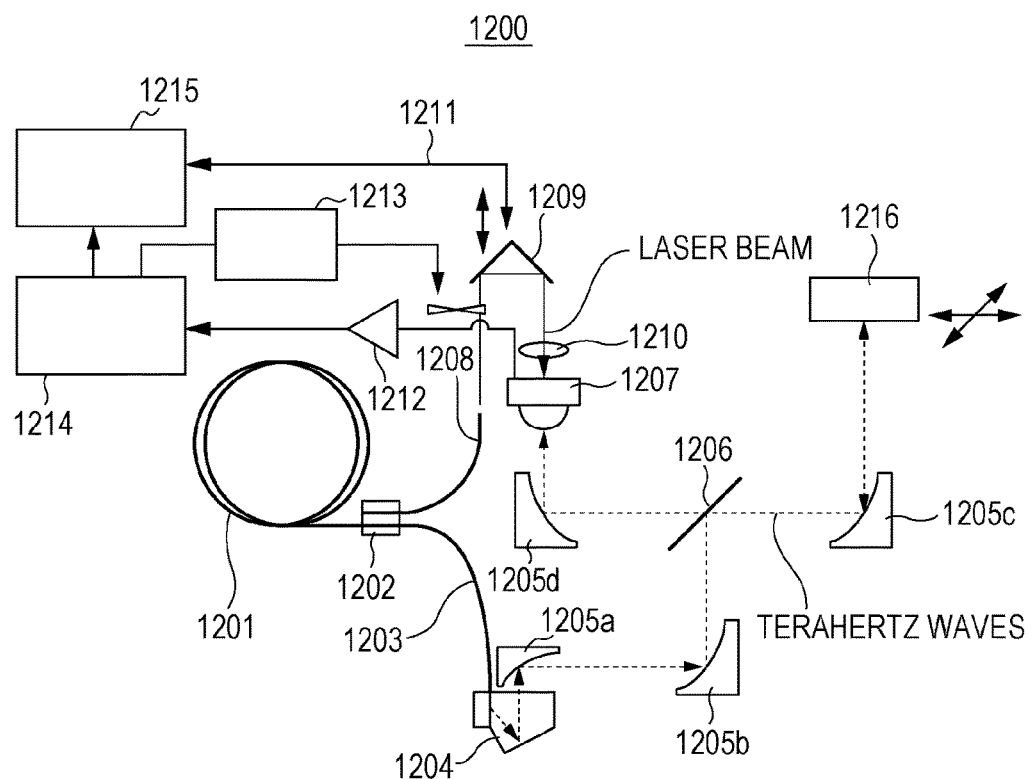
FIGS. 12A and 12B are diagrams for describing the configuration of an information acquiring apparatus according to a seventh embodiment.

FIG. 12A is a configuration diagram of the apparatus 1200. The apparatus 1200 includes a light source 1201, a branching unit 1202, a generating unit 1204, parabolic mirrors 1205a through 1205d, a beam splitter 1206, a detecting unit 1207, an optical delay 1209, an amplifying unit 1212, a modulating unit 1213, a signal acquiring unit 1214, and a processing unit 1215.

The light source 1201 generates light, and includes an optical fiber. The light source 1201 according to the present embodiment outputs femtosecond laser (hereinafter referred to as "laser light").

The laser light output from the light source 1201 is branched into two at the branching unit 1202, with one output thereof passing through an optical fiber 1203 and being input to the generating unit 1204, while the other passes through an optical fiber 1208 and reaches the detecting unit 1207. Note that the optical fibers 1203 and 1208 may include highly nonlinear optical fibers to perform higher solution compression, dispersion optical fiber for pre-chirping to reduce the effects of laser light dispersion from the generating unit 1204 to the detecting unit 1207, or the like. There are also preferably polarization maintaining optical fibers.

The generating unit 1204 is a unit which generates terahertz waves, and includes the element 100 according to the first embodiment. The terahertz waves 1230 are generated by laser light passing through the optical fiber 1203 and entering the crystal 102 of the element 100 serving as the generating unit 1204. The generated terahertz waves 1203 are propagated through the coupling member 103 and externally extracted.

The optical fiber 1203 is preferably configured such that the output of the laser light is no greater than the numerical aperture (NA) of the crystal 102. This can be realized by a method where the tip of the optical fiber 1203 is formed to be a pigtail, or the like. This is to raise the coupling efficiency of input laser light from the optical fiber 1203 to the crystal 102. Space coupling may also be performed using a lens. In these cases, applying a non-reflective coating to the ends of the optical fiber 1203 and crystal 102 enables reduction of Fresnel loss and unnecessary interference noise. The optical fiber 2013 may be bonded to the crystal 102 by direct coupling (butt-coupling) with the NA and mode field diameter being designed to be close to the Na and mode field diameter of the crystal 102. Reflection can be reduced in this case by selecting a suitable adhesive agent.

Note that in a case where a non-polarization-maintaining optical fiber is included in the optical fiber 1203, light source 1201, or the like, the polarization of the laser light input to the generating unit 1204 is preferably stabilized by an inline polarization controller.

The specimen 1216 is irradiated by the terahertz waves 1230 from the generating unit 1204 which pass through an optical system including parabolic mirrors 1205a and 1205b, the beam splitter 1206, and a parabolic mirror 1205c. the terahertz waves 1230 which have reflected at the specimen 1216 are collected at a parabolic mirror 1205d and input to the detecting unit 1207.

On the other hand, the laser light passing through the optical fiber 1208 passes through the optical delay 1209 and lens 1210 and is input to the detecting unit 1207 from the opposite side as to the terahertz waves 1230 reflected at the specimen 1216. Hereinafter in the present specification, the laser light entering the detecting unit 1207 will be referred to as "probe light".

The optical delay 1209 is a portion where the timing of detection of the terahertz waves 1230 is adjusted by appropriately changing the difference in the length of the optical paths over which the terahertz waves 1230 and the probe light travel to enter the detecting unit 1207. A loopback optical system for loopback of the probe light, and a movable portion which moves the loopback optical system, are used in the present embodiment to change the length of the optical path over which the probe light travels to be input to the detecting unit 1207.

The optical delay 1209 is not restricted to the above-described configuration. A rotating system may be applied to the moving portion. Alternatively, a method where the refractive index along the propagation path of the probe light is adjusted to change the optical path length, or the like, may be applied as well. On the other hand, the length of the optical path over which the laser light travels from the light source 1201 to the generating unit 1204 may be changed instead of the path over which the probe light travels, using a method such as described above.

The detecting unit 1207 is the part where the terahertz waves 1230 are detected, and uses a photoconductive element which has been fabricated by forming a dipole antenna on low-temperature-grown gallium arsenide (GaAs). In a case where the wavelength of the laser light output from the light source 1201 is 1.55 µm, a second harmonic generation (SHG) crystal, which is omitted from illustration, may be disposed on the propagation path of the probe light. Generating second order harmonics using an SHG crystal enables probe light suitable for GaAs excitation to be obtained, thereby enabling highly precise detection.

The SHG crystal used preferably is a crystal of periodically poled lithium niobate (PPLN), around 0.1 mm thick, to maintain the pulse forms of the laser light. Note in that a case where the pulse width is sufficiently small, as in the case of the present embodiment, the fundamental wave may be used as the probe light as it is.

The signals detected at the detecting unit 1207 are subjected to phase-sensitive detection, and the output signals thereof are amplified at the amplifying unit 1212 and forwarded to the signal acquiring unit 1214. An optical chopper 1211 is a part which modulates the probe light so as to perform phase-sensitive detection, and is controlled by the modulating unit 1213.

The signal acquiring unit 1214 is a part which acquires output signals from the detecting unit 1207. The processing unit acquires the time waveform based on the output signals acquired by the signal acquiring unit 1214, and inspects the time waveform, thereby acquiring information regarding the specimen 1216. An image of the internal structure of the specimen 1216 may also be obtained based on the acquired information of the specimen 1216.

If there are portions within the specimen 1216 where the refractive index differs (interfaces), time waveforms of the terahertz waves reflected at the interfaces appear at different positions on the time waveforms in the imaging of the internal structure of the specimen 1216, depending on the depth of the interfaces. Accordingly, one-dimensional scanning of the specimen 1216 enables a tomographic image to be obtained, and two-dimensional scanning of the specimen 1216 enables a three-dimensional image to be obtained.

Figure 12B:
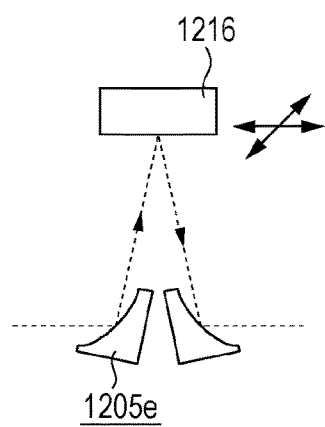
Figure 13:
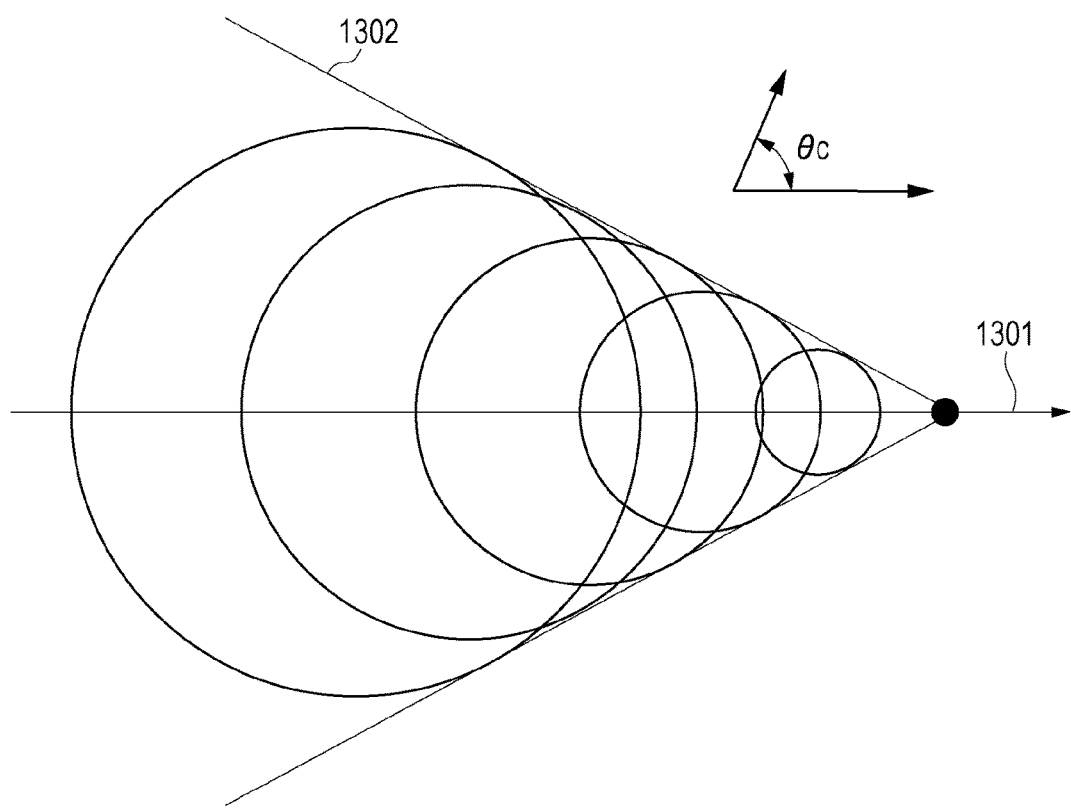
FIG. 13 is a diagram for describing the electro-optical Cherenkov radiation phenomenon.

Note that the terahertz waves 1230 collected at the parabolic mirror 1205c, by which the specimen 1216 is irradiated, and the terahertz waves 1230 reflected at the specimen 1216 and traveling toward the parabolic mirror 1205c, are generally coaxial. Thus, the power of the terahertz waves 1230 decreases due to two terahertz waves 1230 being branched at the beam splitter 1206. Accordingly, an arrangement may be made such as illustrated in FIG. 12B, where one or more parabolic mirrors 1205e are additionally provided to form a non-coaxial configuration. In this case, the incident angle of the terahertz waves 1230 by which the specimen 1216 is irradiated is not 90 degrees, but the output of the detected terahertz waves 1230 can be increased.

While the element 100 according to the first embodiment has been used as the generating unit 1204 in the present embodiment, Any of the terahertz wave generating elements or the like in the first through third embodiments may be used. In a case of using the element according to the third embodiment, there is no need to provide an optical system to guide the terahertz waves 1230 from the generating unit 1204 to the specimen 1216.

While the detecting unit 1207 is used as a photoconductor in the present embodiment, this may be replaced by a terahertz waves detecting element according to the fourth and fifth embodiments, or another terahertz waves detecting element. In a case of using a terahertz waves detecting element according to the fourth and fifth embodiments as the detecting unit 1207, the configuration of the generating unit 1204 is not restricted and a terahertz waves detecting element according to the above-described embodiments may be used, or a known terahertz waves generating element such as a photoconductor may be used. In a case of using the element 1000 according to the fifth embodiment, an optical system to guide the terahertz waves 1230 reflected at the specimen 1216 to the detecting unit 1207 can be omitted.

The generating unit 1204 and detecting unit 1207 may also be replaced by a generating/detecting element such as described in the fifth and sixth embodiments, so as to have a single generating/detecting unit. In this case, the optical system to guide terahertz waves 1230 from the generating unit 1204 to the specimen 1216, and the optical system to guide the terahertz waves 1230 from the specimen 1216 to the detecting unit 1207, can be omitted. Further, while the apparatus 1200 has been described as the terahertz waves 1230 reflected at the specimen 1216 being detected, the terahertz waves 1230 transmitted through the specimen 1216 may be detected instead.

Further, application of the terahertz wave generating elements, terahertz wave detecting elements, and terahertz wave generating/detecting elements, according to the first through seventh embodiments is not restricted to the THz-TDS apparatus according to the present embodiment, and may be applied to other information acquiring apparatuses as well.

Using the element 100 as the generating unit 1204 enables the apparatus 1200 according to the present embodiment to measure the specimen 1216 using terahertz waves with reduced power distribution distortion, which enables measurement with high resolution. Reduction in power distribution distortion means that the power of the terahertz waves by which the specimen 1216 is irradiated is greater, so improved S/N ratio can be expected. Further, the optical system is configured using optical fibers in the present embodiment, so reduction in the size of the apparatus 1200 can be expected.

First Exemplary Embodiment

A more detailed configuration example of the element 100 according to the first embodiment will be described, as a first exemplary embodiment. The length of the waveguide 201 is 10 mm. The core layer 102 included in the waveguide 201 is formed of an MgO-doped LN crystal layer which is 5 µm wide and 3.8 µm thick. An upper clad layer 202 which is 5 µm wide and 2 µm thick is formed upon the core layer 102. The upper clad layer 202 is an optical adhesive agent for bonding the core layer 102 and the coupling member 103 together.

The thickness of the upper clad layer 202 is determined from the wavelength of the generated terahertz waves 105. In a case where the maximum frequency of the terahertz waves 105 is 7 THz, the wavelength of the terahertz waves 105 in free space is approximately 43 µm. AS described above, the thickness of the upper clad layer 202 is preferably $\lambda_{eq}/10$ or less, as described earlier. In a case where the refractive index of a buffer layer is 1.5, $\lambda_{eq}/10=2.85$, so the thickness of the upper clad layer 202 is set to 2 µm so as to be within this thickness range.

High-resistance Si is used for the coupling member 103. The reflecting face 107 of the coupling member 103 has a shape like a conical face with part thereof cut off, and is configured such that the axis 109 of the conical face and the propagation direction of the light 104 agree. At this time, the angle α formed between the propagation direction of the light 104 and the reflecting face 107 is 65 degrees. The size of the coupling member 103 from the input end of the waveguide 201 to an apex 110 of the conical face is 18 mm.

The Cherenkov angle $\theta_{clad}$ in the present embodiment is 50 degrees. The angle i between the terahertz waves 105 and the perpendicular of the reflection face 107 in a case where the terahertz waves 105 are input to the reflecting face 107 (incident angle) is 25 degrees, and the angle j between the terahertz waves 105 reflected at the reflection face 107 and the perpendicular of the reflection face 107 (reflection angle) is also 25 degrees.

The incident light 104 to the crystal 102 is an ultrashort pulse laser of which the peak wavelength is 1.6 μm, the pulse width is 20 fs, average power is 60 mW, and beam diameter (diameter of intensity portion no less than $1/e^2$ of maximum intensity) is 6 μm. Upon light 104 input from the end of the crystal 102 propagating in single mode through the crystal 102, terahertz waves 105 are generated by conically emitted by Cherenkov radiation.

The emitted terahertz waves 105 are propagated through the coupling member 103, and reflected at the reflecting face 107. The total reflection angle at the interface of the high-resistance Si making up the coupling member 103 and the air is approximately 17 degrees, so the terahertz waves 105 are totally reflected at the reflecting face 107. The terahertz waves 105 reflected at the reflecting face 107 are transmitted through the transmission face 108 and emitted to the space outside of the coupling member 103.

According to the element 100 of the present embodiment, terahertz waves with little distortion in power distribution can be obtained while shaping the waveform of the terahertz waves to be almost planar.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

For example, description has been made in the above embodiments regarding a case where the width of the nonlinear optical crystal 102 is small to the point that it can be considered to be a point light source with no width. However, the present invention is not restricted to this, and the present invention can be applied to a case where the nonlinear optical crystal 102 has a substantial width.

In this case, the shape of the reflecting face 107 of the coupling member 103 at a cross-section orthogonal to the propagation direction of light is preferably changed in accordance with the wavefront of the terahertz waves 105 at the face orthogonal to the propagation direction of light. One conceivable example is a form close to an elliptic shape, such as illustrated in FIG. 3D. This shape enables the wavefront to be nearer to a plane, while reducing distortion in power distribution of the terahertz waves reflected at the reflecting face 107.

Also, description has been made in the above embodiments regarding a case where the width of the reflecting face is a straight line in a plane including the propagation direction of light, but may be a curve rather than a straight line. In such a case, the angle α between the reflecting face and the propagation direction of light should be made to be the angle between the tangent of the curve making up the reflecting face and the propagation direction of light.

Also, description has been made in the above embodiments regarding a case where LN is used as the nonlinear optical crystal, but the present invention is not restricted to this, and other nonlinear optical crystals may be used as well. LN has a sufficiently great difference between the refractive index regarding terahertz waves and the refractive index regarding laser light, so terahertz waves generated non-collinearly can be extracted.

However, depending on the nonlinear optical crystal used, this refractive index difference may be so small that the generated terahertz waves are not readily extracted. Such a case can be handled by providing the waveguide 201 so that the nonlinear optical crystal 102 and the coupling member 103 are sufficiently close, and forming the coupling member 103 of a material which has a greater refractive index than the nonlinear optical crystal. This configuration enables conditions for Cherenkov radiation of generated electromagnetic waves ($V_{THz} < V_g$), so that the terahertz waves can be externally extracted.

The length of the waveguide 201 (length in the x direction) of the terahertz wave generating element may be extended to increase the output of terahertz waves. In this case, the size of the coupling member 103 is a so changed to match the length of the waveguide 201, so that more generated terahertz waves can be used.

The substrate 101 also is not restricted to the above embodiments, and various change may be made. For example, the size of the substrate 101 may be reduce, within a range where the waveguide 201 can be meld. The rear face of the substrate 101, which is the face opposite from the face on which the waveguide 201 is formed, can be changed. Specific examples include cutting obliquely so that light reflected on the rear face of the substrate 101 can be prevented from becoming stray light, and in a case where terahertz waves are also irradiated to the rear face of the substrate 101, a prism or lens may be disposed thereat. Various materials may be used, such as Si, resin, and so forth. Further, an arrangement may be made where no substrate 101 is provided.

This application claims the benefit of Japanese Patent Application No. 2013-212295, filed Oct. 9, 2013 and No. 2014-182737, filed Sep. 8, 2014, which are hereby incorporated by reference herein in their entirety.

The invention claimed is:

1. A terahertz wave generating element comprising:
a nonlinear optical crystal configured to generate terahertz waves by light propagating therethrough; and
a coupling member through which the terahertz waves generated by the nonlinear optical crystal propagate;
wherein the coupling member includes a reflecting face configured to reflect at least a part of the terahertz waves generated by the nonlinear optical crystal and a transmission face configured to transmit the terahertz waves reflected at the reflecting face;
wherein the reflecting face is convex in a propagation direction of the terahertz waves generated by the nonlinear optical crystal;
wherein an angle at the coupling member side between the reflecting face and a propagation direction of the light is greater than 90 degrees$-\cos^{-1}(n_g/n_{THz})$ and smaller than 90 degrees at a plane including the propagation direction of the light, where $n_g$ represents a group refractive index of the nonlinear optical crystal at a wavelength of the light, and $n_{THz}$ represents the refractive index of the coupling member at a wavelength of the terahertz waves generated by the nonlinear optical crystal;

and wherein a radius of curvature of the reflecting face, in a reflection region where the terahertz waves generated by the nonlinear optical crystal are reflected, is smaller the farther downstream in the propagation direction of the light.

2. The terahertz wave generating element according to claim 1,
wherein the angle is not less than $\sin^{-1}(n_e/n_{THz})+90$ degrees$-\cos^{-1}(n_g/n_{THz})$, where $n_e$ represents a refractive index of an external matter of the coupling member at the wavelength of the terahertz waves generated by the nonlinear optical crystal.

3. A terahertz wave generating element comprising:
a nonlinear optical crystal configured to generate terahertz waves by light propagating therethrough; and
a coupling member through which the terahertz waves generated by the nonlinear optical crystal propagate;
wherein the coupling member includes a reflecting face configured to reflect at least a part of the terahertz waves generated by the nonlinear optical crystal;
wherein the reflecting face is convex in a propagation direction of the terahertz waves generated by the nonlinear optical crystal;
wherein an angle at the coupling member side between the reflecting face and a propagation direction of the light is not less than $\sin^{-1}(n_e/n_{THz})+90$ degrees$-\cos^{-1}(n_g/n_{THz})$ and smaller than 90 degrees at a plane including the propagation direction of the light, where $n_g$ represents a group refractive index of the nonlinear optical crystal at a wavelength of the light, $n_e$ represents a refractive index of an external matter of the coupling member at the wavelength of the terahertz waves generated by the nonlinear optical crystal, and $n_{THz}$ represents the refractive index of the coupling member at a wavelength of the terahertz waves generated by the nonlinear optical crystal;
and wherein a radius of curvature of the reflecting face, in a reflection region where the terahertz waves generated by the nonlinear optical crystal are reflected, is smaller the farther downstream in the propagation direction of the light.

4. The terahertz wave generating element according to claim 1,
wherein the angle is 90 degrees$-\cos^{-1}(n_g/n_{THz})/2 \pm \lambda/8$, where $\lambda$ represents the wavelength of the terahertz waves generated by the nonlinear optical crystal.

5. The terahertz wave generating element according to claim 1,
wherein the terahertz waves generated by the nonlinear optical crystal are totally reflected at the reflecting face.

6. The terahertz wave generating element according to claim 1,
wherein the reflecting face includes a part of a curve formed by rotating a straight line or a curve of which the axis of rotation is the propagation direction of the light.

7. The terahertz wave generating element according to claim 1,
wherein the reflecting face includes a part of a conical face of which the axis is the propagation direction of the light.

8. The terahertz wave generating element according to claim 1,
wherein at least part of a cross-section of the reflecting face at a plane orthogonal to the propagation direction of the light through the coupling member is a part of a circle or ellipse.

9. The terahertz wave generating element according to claim 1,
wherein the plane including the propagation direction of the light is perpendicular to the surface of the nonlinear optical crystal.

10. The terahertz wave generating element according to claim 1, further comprising:
a waveguide;
wherein the waveguide includes the nonlinear optical crystal, and a clad layer which is disposed between the nonlinear optical crystal and the coupling member and which has a refractive index lower than the refractive index of the nonlinear optical crystal at the wavelength of the light.

11. The terahertz wave generating element according to claim 1,
wherein the width of the nonlinear optical crystal is smaller than the wavelength of the terahertz waves generated by the nonlinear optical crystal.

12. The terahertz wave generating element according to claim 1,
wherein the nonlinear optical crystal is configured so that the terahertz waves generated by the nonlinear optical crystal are input again, whereby a propagation state of light different from the light changes, whereby the terahertz waves generated by the nonlinear optical crystal are detected using the light of which the propagation state has changed.

13. A terahertz wave detecting element comprising:
a nonlinear optical crystal configured to change a propagation state of light by input of terahertz waves; and
a coupling member configured to guide the terahertz waves to the nonlinear optical crystal;
wherein the coupling member includes a transmission face configured to transmit the terahertz waves and a reflecting face configured to reflect at least a part of the terahertz waves transmitted through the transmission face;
wherein the reflecting face is convex in a direction opposite to the propagation direction of the terahertz waves input to the nonlinear optical crystal;
wherein an angle at the coupling member side between the reflecting face and a propagation direction of the light is greater than 90 degrees$-\cos^{-1}(n_g/n_{THz})$ and smaller than 90 degrees at a plane including the propagation direction of the light, where $n_g$ represents a group refractive index of the nonlinear optical crystal at a wavelength of the light, and $n_{THz}$ represents the refractive index of the coupling member at a wavelength of the terahertz waves generated by the nonlinear optical crystal;
and wherein a radius of curvature of the reflecting face, in a reflection region where the terahertz waves generated by the nonlinear optical crystal are reflected, is greater the farther downstream in the propagation direction of the light.

14. A terahertz wave detecting element comprising:
a nonlinear optical crystal configured to change a propagation state of light by input of terahertz waves; and
a coupling member configured to guide the terahertz waves to the nonlinear optical crystal;

wherein the coupling member includes a reflecting face configured to reflect at least a part of the terahertz waves input to the nonlinear optical crystal;

wherein the reflecting face is convex in a direction opposite to the propagation direction of the terahertz waves input to the nonlinear optical crystal;

wherein an angle at the coupling member side between the reflecting face and a propagation direction of the light is not less than $\sin^{-1}(n_e/n_{THz})+90$ degrees$-\cos^{-1}(n_g/n_{THz})$ and smaller than 90 degrees at a plane including the propagation direction of the light, where $n_g$ represents a group refractive index of the nonlinear optical crystal at a wavelength of the light, and $n_{THz}$ represents the refractive index of the coupling member at a wavelength of the terahertz waves generated by the nonlinear optical crystal;

and wherein a radius of curvature of the reflecting face, in a reflection region where the terahertz waves generated by the nonlinear optical crystal are reflected, is greater the farther downstream in the propagation direction of the light.

15. An information acquisition apparatus configured to irradiate a specimen with terahertz waves and acquire information of the specimen, the apparatus comprising:
a generating unit configured to generate terahertz waves; and
a detecting unit configured to detect the terahertz waves which have transmitted or reflected at the specimen;
wherein the generating unit includes the terahertz wave generating element according to claim 1.

16. The information acquisition apparatus according to claim 15,
wherein the generating unit and detecting unit are configured integrally, in which the terahertz wave generating element functions as the generating unit and the detecting unit.

17. An information acquisition apparatus configured to irradiate a specimen with terahertz waves and acquire information of the specimen, the apparatus comprising:
a generating unit configured to generate terahertz waves; and
a detecting unit configured to detect the terahertz waves from the specimen;
wherein the detecting unit includes the terahertz wave detecting element according to claim 13.

18. A terahertz wave generating element comprising:
a crystal including at least one selected from a group consisting of LiNbOx, LiTaOx, NbTaOx, KTP, DAST, ZnTe, GaSe, and GaAs; and
a coupling member through which terahertz waves propagate, the terahertz waves being generated from the crystal as a result of light propagating through the crystal;
wherein the coupling member includes a reflecting face configured to reflect at least a part of the terahertz waves generated from the crystal and a transmission face configured to transmit the terahertz waves reflected at the reflecting face;
wherein the reflecting face includes a part of a conical face that has an apex on a downstream side of a propagation direction of the light.

19. The terahertz wave generating element according to claim 18,
wherein an angle at the coupling member side between the reflecting face and the propagation direction of the light is greater than 90 degrees$-\theta_c$ and smaller than 90 degrees at a plane including the propagation direction of the light, where $\theta_c$ represents the Cherenkov angle at the coupling member.

20. The terahertz wave generating element according to claim 18,
wherein the terahertz waves generated from the crystal are totally reflected at the reflecting face.

21. The terahertz wave generating element according to claim 18,
wherein the axis of the conical face is oriented in the propagation direction of the light.

* * * * *